(12) United States Patent
Angel et al.

(10) Patent No.: US 10,478,282 B2
(45) Date of Patent: *Nov. 19, 2019

(54) REDUCED PROFILE CENTRAL VENOUS ACCESS CATHETER WITH VENA CAVA FILTER AND METHOD

(71) Applicant: Mermaid Medical Vascular, ApS, Stenlose (DK)

(72) Inventors: Luis F. Angel, San Antonio, TX (US); Jeffrey N. Steinmetz, Arvada, CO (US)

(73) Assignee: Mermaid Medical Vascular, ApS, Stenlose (DK)

( * ) Notice: Subject to any disclaimer, the term of this patent is extended or adjusted under 35 U.S.C. 154(b) by 280 days.

This patent is subject to a terminal disclaimer.

(21) Appl. No.: 15/634,662

(22) Filed: Jun. 27, 2017

(65) Prior Publication Data

US 2017/0354490 A1      Dec. 14, 2017

Related U.S. Application Data

(63) Continuation of application No. 13/786,361, filed on Mar. 5, 2013, now Pat. No. 9,687,333, which is a
(Continued)

(51) Int. Cl.
*A61F 2/01* (2006.01)
*A61M 25/00* (2006.01)

(52) U.S. Cl.
CPC ......... *A61F 2/013* (2013.01); *A61M 25/0029* (2013.01); *A61F 2002/016* (2013.01);
(Continued)

(58) Field of Classification Search
CPC .......... A61F 2002/016; A61F 2230/008; A61F 2230/0093; A61F 2/013; A61M 2025/0003; A61M 2025/0036; A61M 2025/004
(Continued)

(56) References Cited

U.S. PATENT DOCUMENTS

| 3,671,979 A | 6/1972 | Moulopouios ................ 3/1 |
| 4,405,313 A | 9/1983 | Sisley et al. .............. 604/43 |

(Continued)

FOREIGN PATENT DOCUMENTS

| WO | WO 1996/030073 | 10/1996 | ........... A61M 29/00 |
| WO | WO 1997/017100 | 5/1997 | ........... A61M 29/00 |

(Continued)

OTHER PUBLICATIONS

Decousus, et al., "A clinical trial of vena cava filters in the prevention of pulmonary embolism in patients with proximal deep-vein thrombosis" *N Engl J Med* 338(7): 409-415 (1998).
(Continued)

*Primary Examiner* — Katherine M Shi
(74) *Attorney, Agent, or Firm* — David G. Rosenbaum; Benjamin D. Rotman; Rosenbaum IP, P.C.

(57) ABSTRACT

A central access vena cava filter catheter having a multi-lumen catheter body with plural longitudinally extending parallel lumens within the single catheter body, a vena cava filter member disposed at a distal end of the catheter body and an outer sheath concentrically disposed about the multi-lumen catheter body and the vena cava filter member. The vena cava filter member may be removably coupled to the multi-lumen catheter for temporary placement and retrieval under recommended indications.

18 Claims, 12 Drawing Sheets

Related U.S. Application Data continuation-in-part of application No. 11/849,225, filed on Aug. 31, 2007, now Pat. No. 8,668,712, and a continuation-in-part of application No. 12/684,839, filed on Jan. 8, 2010, now Pat. No. 8,613,753, and a continuation-in-part of application No. 13/091,826, filed on Apr. 21, 2011, now Pat. No. 8,777,977.

(52) U.S. Cl.
CPC . *A61F 2230/008* (2013.01); *A61F 2230/0093* (2013.01); *A61M 2025/0002* (2013.01); *A61M 2025/0003* (2013.01); *A61M 2025/004* (2013.01); *A61M 2025/0036* (2013.01); *A61M 2205/3523* (2013.01)

(58) Field of Classification Search
USPC .......................................................... 606/200
See application file for complete search history.

(56) References Cited

U.S. PATENT DOCUMENTS

| | | | |
|---|---|---|---|
| 4,901,731 A | 2/1990 | Millar | 128/675 |
| 4,921,479 A | 5/1990 | Grayzel | 604/53 |
| 4,969,891 A | 11/1990 | Gewertz | 606/200 |
| 5,046,503 A | 9/1991 | Schneiderman | 128/692 |
| 5,053,008 A | 10/1991 | Bajaj | 604/104 |
| 5,112,347 A | 5/1992 | Taheri | 606/200 |
| 5,163,928 A | 11/1992 | Hobbs et al. | 604/281 |
| 5,201,757 A | 4/1993 | Heyn et al. | 606/200 |
| 5,549,626 A | 8/1996 | Miller et al. | 606/200 |
| 5,556,390 A | 9/1996 | Hicks | 604/280 |
| 5,569,215 A | 10/1996 | Crocker | 604/264 |
| 5,624,596 A | 4/1997 | McNamara et al. | 604/93 |
| 5,707,389 A | 1/1998 | Louw et al. | 606/194 |
| 5,713,917 A * | 2/1998 | Leonhardt | A61M 25/10184 606/194 |
| 5,715,829 A | 2/1998 | Cori et al. | 128/673 |
| 5,766,151 A | 6/1998 | Valley et al. | 604/96 |
| 5,769,816 A | 6/1998 | Barbut et al. | 604/96 |
| 5,791,341 A | 8/1998 | Bullard | 128/207.15 |
| 5,795,322 A | 8/1998 | Boudewijn | 604/22 |
| 5,795,325 A | 8/1998 | Valley et al. | 604/53 |
| 5,797,920 A | 8/1998 | Kim | 606/108 |
| 5,814,064 A | 9/1998 | Daniel et al. | 606/200 |
| 5,817,072 A | 10/1998 | Lampropoulos et al. | 604/264 |
| 5,833,650 A | 11/1998 | Imran | 604/53 |
| 5,848,964 A | 12/1998 | Samuels | 600/200 |
| 5,879,499 A | 3/1999 | Corvi | 156/175 |
| 5,893,868 A | 4/1999 | Hanson et al. | 606/198 |
| 5,925,016 A | 7/1999 | Chornenky et al. | 604/96 |
| 5,947,994 A | 9/1999 | Louw et al. | 606/200 |
| 5,947,995 A | 9/1999 | Samuels | 606/200 |
| 5,954,742 A | 9/1999 | Osypka | 606/198 |
| 5,976,172 A | 11/1999 | Homsma et al. | 606/200 |
| 5,980,478 A | 11/1999 | Gorsuch et al. | 604/4 |
| 5,980,555 A | 11/1999 | Barbut et al. | 600/200 |
| 5,989,281 A | 11/1999 | Barbut et al. | 606/200 |
| 6,007,544 A | 12/1999 | Kim | 606/108 |
| 6,036,654 A | 3/2000 | Quinn et al. | 600/526 |
| 6,051,014 A | 4/2000 | Jang | 606/200 |
| 6,083,198 A * | 7/2000 | Afzal | A61M 25/007 604/101.01 |
| 6,086,605 A | 7/2000 | Barbut et al. | 606/200 |
| 6,090,097 A | 7/2000 | Barbut et al. | 604/511 |
| 6,117,154 A | 9/2000 | Barbut et al. | 606/181 |
| 6,135,991 A | 10/2000 | Muni et al. | 604/509 |
| 6,136,016 A | 10/2000 | Barbut et al. | 606/200 |
| 6,152,909 A | 11/2000 | Bagaoisan et al. | 604/523 |
| 6,165,179 A | 12/2000 | Cathcart et al. | 606/108 |
| 6,171,328 B1 | 1/2001 | Addis | 606/200 |
| 6,178,968 B1 | 1/2001 | Louw et al. | 128/898 |
| 6,231,544 B1 | 3/2001 | Tsugita et al. | 604/104 |
| 6,224,627 B1 | 5/2001 | Armstrong et al. | 623/1.23 |
| 6,235,045 B1 | 5/2001 | Barbut et al. | 606/200 |
| 6,251,093 B1 | 6/2001 | Valley et al. | 604/96 |
| 6,270,477 B1 | 8/2001 | Bagaoisan et al. | 604/96.01 |
| 6,277,138 B1 | 8/2001 | Levinson et al. | 606/200 |
| 6,287,321 B1 | 9/2001 | Jang | 606/200 |
| 6,315,792 B1 | 11/2001 | Armstrong et al. | 623/1.13 |
| 6,336,934 B1 | 1/2002 | Gilson et al. | 606/200 |
| 6,344,049 B1 | 2/2002 | Levinson et al. | 606/200 |
| 6,344,053 B1 | 2/2002 | Boneau | 623/1.11 |
| 6,361,545 B1 * | 3/2002 | Macoviak | A61B 17/12109 606/151 |
| 6,379,373 B1 * | 4/2002 | Sawhney | A61B 17/12022 606/193 |
| 6,383,196 B1 | 5/2002 | Leslie et al. | 606/114 |
| 6,423,086 B1 | 7/2002 | Barbut et al. | 606/200 |
| 6,432,122 B1 | 8/2002 | Gilson et al. | 606/200 |
| 6,443,971 B1 | 9/2002 | Boylan et al. | 606/200 |
| 6,454,741 B1 | 9/2002 | Muni et al. | 604/96.01 |
| 6,468,291 B2 | 10/2002 | Bates et al. | 606/200 |
| 6,482,171 B1 | 11/2002 | Corvi et al. | 604/96.01 |
| 6,511,503 B1 | 1/2003 | Burkett et al. | 623/1.11 |
| 6,537,294 B1 | 3/2003 | Boyle et al. | 606/200 |
| 6,537,296 B2 | 3/2003 | Levinson et al. | 606/200 |
| 6,537,297 B2 | 3/2003 | Tsugita et al. | 606/200 |
| 6,544,279 B1 | 4/2003 | Hopkins et al. | 606/200 |
| 6,547,788 B1 | 4/2003 | Maguire et al. | 604/41 |
| 6,561,996 B1 | 5/2003 | Gorsuch | 604/6.09 |
| 6,569,148 B2 | 5/2003 | Bagaoisan et al. | 604/509 |
| 6,585,639 B1 | 7/2003 | Kotmel et al. | 600/116 |
| 6,589,264 B1 | 7/2003 | Barbut et al. | 606/200 |
| 6,592,546 B1 | 7/2003 | Barbut et al. | 604/96.01 |
| 6,596,011 B2 | 7/2003 | Johnson et al. | 606/200 |
| 6,616,680 B1 | 9/2003 | Theilen | 606/200 |
| 6,623,507 B2 | 9/2003 | Saleh | 606/200 |
| 6,635,070 B2 | 10/2003 | Leeflang et al. | 606/200 |
| 6,669,708 B1 | 12/2003 | Nissenbaum et al. | 606/153 |
| 6,685,722 B1 | 2/2004 | Rosenbluth et al. | 606/200 |
| 6,689,148 B2 | 2/2004 | Sawhney et al. | 606/193 |
| 6,692,512 B2 | 2/2004 | Jang | 606/200 |
| 6,726,651 B1 | 4/2004 | Robinson et al. | 604/101.01 |
| 6,726,702 B2 | 4/2004 | Khosravi | 606/200 |
| 6,749,619 B2 | 6/2004 | Ouriel et al. | 606/200 |
| 6,755,183 B2 | 6/2004 | Ouriel et al. | 604/537 |
| 6,755,813 B2 | 6/2004 | Ouriel et al. | 604/537 |
| 6,780,193 B2 | 8/2004 | Leslie et al. | 606/114 |
| 6,805,692 B2 | 10/2004 | Muni et al. | 604/509 |
| 6,869,431 B2 | 3/2005 | Maguire et al. | 604/41 |
| 6,885,115 B2 | 4/2005 | Hatori et al. | 307/80 |
| 6,887,257 B2 | 5/2005 | Salahieh et al. | 606/200 |
| 6,913,600 B2 | 7/2005 | Valley et al. | 604/509 |
| 6,986,778 B2 | 1/2006 | Zadno-Azizi | 606/200 |
| 7,011,672 B2 | 3/2006 | Barbut et al. | 606/200 |
| 7,060,082 B2 | 6/2006 | Goll et al. | 606/200 |
| 7,108,708 B2 | 9/2006 | Cheng et al. | 606/200 |
| 7,125,414 B2 | 10/2006 | Blackledge et al. | 606/200 |
| 7,144,408 B2 | 12/2006 | Keegan et al. | 606/200 |
| 7,150,737 B2 | 12/2006 | Purdy et al. | 604/506 |
| 7,153,320 B2 | 12/2006 | Euteneuer et al. | 606/200 |
| 7,163,520 B2 | 1/2007 | Bernard et al. | 604/6.9 |
| 7,166,570 B2 | 1/2007 | Hunter et al. | 514/2 |
| 7,220,270 B2 | 5/2007 | Sawhney et al. | 606/193 |
| 7,261,727 B2 | 8/2007 | Thielen | 606/200 |
| 7,544,202 B2 | 6/2009 | Cartier et al. | 606/200 |
| 7,985,236 B2 | 7/2011 | Pepper | 606/194 |
| 8,231,519 B2 | 7/2012 | Reichenbach et al. | 600/16 |
| 2001/0001812 A1 | 5/2001 | Valley et al. | 604/96.01 |
| 2001/0031981 A1 | 10/2001 | Evan et al. | 606/200 |
| 2002/0062134 A1 | 5/2002 | Barbut et al. | 606/200 |
| 2002/0072730 A1 | 6/2002 | McGill et al. | 604/525 |
| 2002/0082525 A1 | 6/2002 | Oslund et al. | 600/585 |
| 2002/0082636 A1 | 6/2002 | Sawhney et al. | 606/193 |
| 2002/0091407 A1 | 7/2002 | Zadno-Azizi et al. | 606/200 |
| 2002/0107479 A1 | 8/2002 | Bates et al. | 604/96.01 |
| 2002/0107506 A1 | 8/2002 | McGuckin, Jr. et al. | 604/523 |
| 2002/0115983 A1 | 8/2002 | Sekino et al. | 604/528 |
| 2002/0165575 A1 | 11/2002 | Saleh | 606/200 |
| 2002/0188313 A1 | 12/2002 | Johnson et al. | 606/200 |
| 2003/0009146 A1 | 1/2003 | Muni et al. | 604/500 |
| 2003/0032941 A1 | 2/2003 | Boyle et al. | 604/533 |

(56) References Cited

U.S. PATENT DOCUMENTS

| | | | |
|---|---|---|---|
| 2003/0050600 A1 | 3/2003 | Reesemann et al. | 604/101.01 |
| 2003/0093110 A1 | 5/2003 | Vale | 606/200 |
| 2003/0097082 A1 | 5/2003 | Purdy et al. | 606/594 |
| 2003/0097094 A1 | 5/2003 | Ouriel et al. | 604/93.01 |
| 2003/0125764 A1 | 7/2003 | Brady et al. | 606/200 |
| 2003/0176889 A1 | 9/2003 | Boyle et al. | 606/200 |
| 2003/0187495 A1 | 10/2003 | Cully et al. | 623/1.15 |
| 2003/0203031 A1 | 10/2003 | Shah | 424/485 |
| 2003/0208222 A1 | 11/2003 | Zadno-Azizi | 606/194 |
| 2003/0212429 A1 | 11/2003 | Keegan et al. | 606/200 |
| 2003/0212434 A1 | 11/2003 | Thielen | 606/200 |
| 2003/0233117 A1 | 12/2003 | Adams et al. | 606/200 |
| 2004/0006367 A1 | 1/2004 | Johnson et al. | 606/200 |
| 2004/0011740 A1 | 1/2004 | Bernard et al. | 210/646 |
| 2004/0044302 A1 | 3/2004 | Bernard et al. | 604/6.09 |
| 2004/0102806 A1 | 5/2004 | Broome et al. | 606/200 |
| 2004/0125764 A1 | 7/2004 | Brady et al. | 606/200 |
| 2004/0153112 A1 | 8/2004 | Nissenbaum et al. | 606/185 |
| 2004/0158276 A1 | 8/2004 | Barbut et al. | 606/200 |
| 2004/0162576 A1 | 8/2004 | Barbut et al. | 606/200 |
| 2004/0199177 A1 | 10/2004 | Kim | 606/108 |
| 2004/0220612 A1 | 11/2004 | Swainston et al. | 606/200 |
| 2004/0236170 A1 | 11/2004 | Kim | 600/16 |
| 2004/0254528 A1 | 12/2004 | Adams et al. | 604/96.01 |
| 2005/0021075 A1 | 1/2005 | Bonnette et al. | 606/200 |
| 2005/0027236 A1 | 2/2005 | Douk et al. | 604/40 |
| 2005/0038503 A1 | 2/2005 | Greenhalgh et al. | 623/1.42 |
| 2005/0080445 A1 | 4/2005 | Sawhney et al. | 606/193 |
| 2005/0085769 A1 | 4/2005 | MacMahon et al. | 604/96.01 |
| 2005/0085841 A1 | 4/2005 | Eversull et al. | 606/190 |
| 2005/0107817 A1 | 5/2005 | White et al. | 606/191 |
| 2005/0113862 A1 | 5/2005 | Besselink et al. | 606/200 |
| 2005/0133046 A1 | 6/2005 | Becker et al. | 128/898 |
| 2005/0142163 A1 | 6/2005 | Hunter et al. | 424/423 |
| 2005/0145258 A1 | 7/2005 | Dong | 128/898 |
| 2005/0147562 A1 | 7/2005 | Hunter et al. | 424/9.5 |
| 2005/0147599 A1 | 7/2005 | Hunter et al. | 424/94.63 |
| 2005/0147643 A1 | 7/2005 | Hunter et al. | 424/423 |
| 2005/0148512 A1 | 7/2005 | Hunter et al. | 514/12 |
| 2005/0148997 A1 | 7/2005 | Valley et al. | 424/509 |
| 2005/0158274 A1 | 7/2005 | Hunter et al. | 424/78.38 |
| 2005/0169958 A1 | 8/2005 | Hunter et al. | 424/423 |
| 2005/0169959 A1 | 8/2005 | Hunter et al. | 424/423 |
| 2005/0175657 A1 | 8/2005 | Hunter et al. | 424/422 |
| 2005/0177186 A1 | 8/2005 | Cully et al. | 606/200 |
| 2005/0186247 A1 | 8/2005 | Hunter et al. | 424/423 |
| 2005/0191248 A1 | 9/2005 | Hunter et al. | 424/50 |
| 2005/0192620 A1 | 9/2005 | Cully et al. | 606/200 |
| 2005/0197624 A1 | 9/2005 | Goodson, IV et al. | 604/96.01 |
| 2005/0205097 A1 | 9/2005 | Kyle, Jr. | 128/207.14 |
| 2005/0245962 A1 | 11/2005 | Adams et al. | 606/194 |
| 2005/0261733 A1 | 11/2005 | Cheng et al. | 606/200 |
| 2005/0267408 A1 | 12/2005 | Grandt et al. | 604/103.04 |
| 2005/0267442 A1 | 12/2005 | Von Depen | 604/509 |
| 2005/0277976 A1 | 12/2005 | Galdonik et al. | 606/200 |
| 2005/0283182 A1 | 12/2005 | Pierce et al. | 606/200 |
| 2006/0135961 A1 | 6/2006 | Rosenman et al. | 606/108 |
| 2006/0189921 A1 | 8/2006 | Galdonik et al. | 604/27 |
| 2006/0190025 A1 | 8/2006 | Lehe et al. | 606/200 |
| 2006/0200191 A1 | 9/2006 | Zadno-Azizi | 606/200 |
| 2006/0229657 A1 | 10/2006 | Wasicek et al. | 606/200 |
| 2006/0240063 A9 | 10/2006 | Hunter et al. | 424/423 |
| 2006/0240064 A9 | 10/2006 | Hunter et al. | 424/423 |
| 2006/0241675 A1 | 10/2006 | Johnson et al. | 606/200 |
| 2006/0241676 A1 | 10/2006 | Johnson et al. | 606/200 |
| 2006/0241677 A1 | 10/2006 | Johnson et al. | 606/200 |
| 2006/0241678 A1 | 10/2006 | Johnson et al. | 606/200 |
| 2006/0241679 A1 | 10/2006 | Johnson et al. | 606/200 |
| 2006/0241680 A1 | 10/2006 | Johnson et al. | 606/200 |
| 2006/0248871 A1 | 11/2006 | Johnson et al. | 57/58.83 |
| 2006/0271098 A1 | 11/2006 | Peacock, III | 606/200 |
| 2007/0006441 A1 | 1/2007 | McNiven et al. | 29/508 |
| 2007/0016132 A1 | 1/2007 | Oepen et al. | 604/96.01 |
| 2007/0016165 A1 | 1/2007 | Von Oepen et al. | 604/525 |
| 2007/0021771 A1 | 1/2007 | Oepen et al. | 606/194 |
| 2007/0055365 A1 | 3/2007 | Greenberg et al. | 623/1.44 |
| 2007/0060942 A2 | 3/2007 | Zadno-Azizi | 606/194 |
| 2007/0065484 A1 | 3/2007 | Chudzik et al. | 424/426 |
| 2007/0083188 A1 | 4/2007 | Grandt et al. | 604/524 |
| 2007/0123838 A1 | 5/2007 | Bernard et al. | 604/500 |
| 2007/0129752 A1 | 6/2007 | Webler et al. | 606/200 |
| 2007/0129753 A1 | 6/2007 | Quinn et al. | 606/200 |
| 2007/0191717 A1 | 8/2007 | Rosen et al. | 600/485 |
| 2007/0208374 A1 | 9/2007 | Boyle et al. | 606/200 |
| 2007/0244503 A1 | 10/2007 | Casey et al. | 606/200 |
| 2007/0293930 A1 | 12/2007 | Wang et al. | 623/1.11 |
| 2008/0051671 A1 | 2/2008 | Broome et al. | 600/504 |
| 2009/0043332 A1 | 2/2009 | Sullivan et al. | 606/200 |
| 2009/0062480 A1 | 3/2009 | Angel | 606/200 |
| 2012/0158037 A1 | 6/2012 | Angel et al. | 606/200 |

FOREIGN PATENT DOCUMENTS

| | | | | |
|---|---|---|---|---|
| WO | WO 1997/042879 | 11/1997 | | A61B 17/00 |
| WO | WO 1998/024501 | 6/1998 | | A61M 25/00 |
| WO | WO 1998/046297 | 10/1998 | | A61M 29/00 |
| WO | WO 1999/065420 | 12/1999 | | A61F 2/06 |
| WO | WO 2000/009190 | 2/2000 | | A61M 25/00 |
| WO | WO 2001/013983 | 3/2001 | | A61M 25/00 |
| WO | WO 2001/037921 | 5/2001 | | A61M 29/00 |
| WO | WO 2001/065936 | 9/2001 | | C12N 11/04 |
| WO | WO 2002/030271 | 4/2002 | | |
| WO | WO 2002/039878 | 5/2002 | | |
| WO | WO 2002/040090 | 5/2002 | | A61M 29/00 |
| WO | WO 2003/015859 | 2/2003 | | A61M 25/06 |
| WO | WO 2003/084437 | 10/2003 | | |
| WO | WO 2004/014240 | 2/2004 | | A61B 17/12 |
| WO | WO 2004/054650 | 7/2004 | | A61M 17/12 |
| WO | WO 2004/060465 | 7/2004 | | A61M 25/00 |
| WO | WO 2004/098674 | 11/2004 | | A61M 2/03 |
| WO | WO 2005/011786 | 2/2005 | | A61M 25/00 |
| WO | WO 2005/023358 | 3/2005 | | A61M 25/00 |
| WO | WO 2005/046746 | 5/2005 | | A61B 17/11 |
| WO | WO 2005/058384 | 6/2005 | | A61L 29/00 |
| WO | WO 2005/065079 | 7/2005 | | A61F 2/02 |
| WO | WO 2005/074520 | 8/2005 | | |
| WO | WO 2005/091910 | 10/2005 | | |
| WO | WO 2005/118044 | 12/2005 | | A61M 25/00 |
| WO | WO 2005/118045 | 12/2005 | | A61M 25/00 |
| WO | WO 2005/118050 | 12/2005 | | A61M 29/00 |
| WO | WO 2006/065949 | 6/2006 | | A61F 11/10 |
| WO | WO 2006/074163 | 7/2006 | | B01D 71/06 |
| WO | WO 2006/089178 | 8/2006 | | A61M 25/00 |
| WO | WO 2006/104591 | 10/2006 | | A61M 25/00 |
| WO | WO 2006/105065 | 10/2006 | | A61F 2/01 |
| WO | WO 2006/116636 | 11/2006 | | A61F 2/06 |
| WO | WO 2006/127929 | 11/2006 | | A61M 29/00 |
| WO | WO 2007/035865 | 3/2007 | | A61M 27/00 |
| WO | WO 2007/035885 | 3/2007 | | A61L 21/20 |
| WO | WO 2009/029861 | 3/2009 | | A61M 5/00 |

OTHER PUBLICATIONS

Extended Search Report from corresponding foreign application, EP 08799012.3, pp. 1-7 (Jun. 6, 2011).

Greenfield, L., et al., "A new intracaval filter permitting continued flow and resolution of emboli" *Surgery* 73(4): 599-606 (1973).

Lin, et al., "Vena caval filters in the treatment of acute DVT" *Endovascular Today* Jan. 40-50 (2005).

Mobin-Uddin, et al., "Experimental prevention of myocardial infarction by bronchial collateral circulation" *JAMA* 208(2): 301-306 (1969).

PCT International Search Report from corresponding PCT international application, PCT/US2008/074885, pp. 1-3 (dated Nov. 26, 2008).

PCT International Search Report from corresponding PCT international application, PCT/US2011/020599, pp. 1-7 (dated Oct. 31, 2011).

PCT International Search Report from corresponding PCT international application, PCT/US2014/017170, pp. 1-6 (dated Jun. 8, 2014).

(56) References Cited

OTHER PUBLICATIONS

PCT Written Opinion from corresponding PCT international application, PCT/US2008/074885, pp. 1-8 (dated Nov. 26, 2008).
PCT Written Opinion from corresponding PCT international application, PCT/US2011/020599, pp. 1-5 (dated Oct. 31, 2011).
PCT Written Opinion from corresponding PCT international application, PCT/US2014/017170, pp. 1-12 (dated Jun. 8, 2014).
Official Action issued in corresponding foreign application, AU 2013205328, pp. 1-4 (dated Jan. 20, 2015).
Official Action issued in corresponding foreign application, AU 2013205329, pp. 1-4 (dated Jan. 21, 2015).
European Search Report issued in corresponding foreign application, pp. 1-8 (dated Nov. 23, 2016).

* cited by examiner

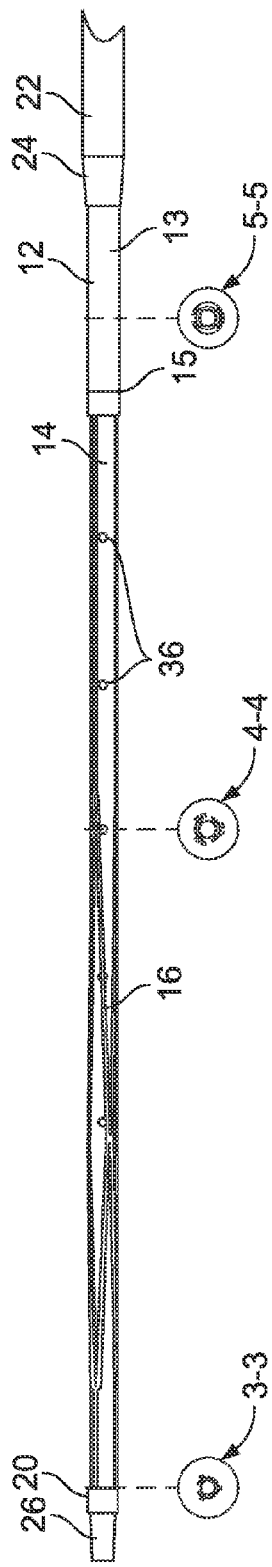
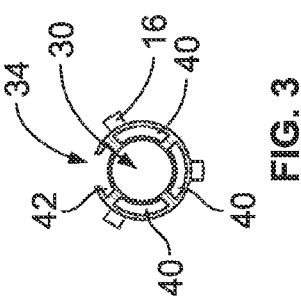

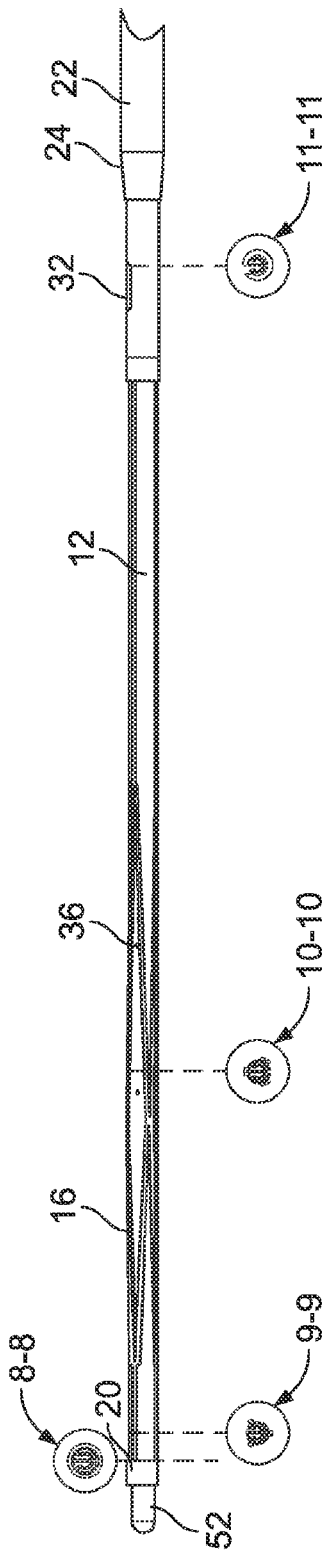
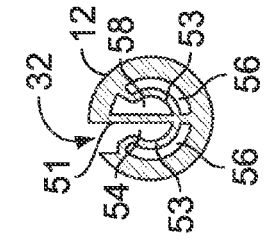
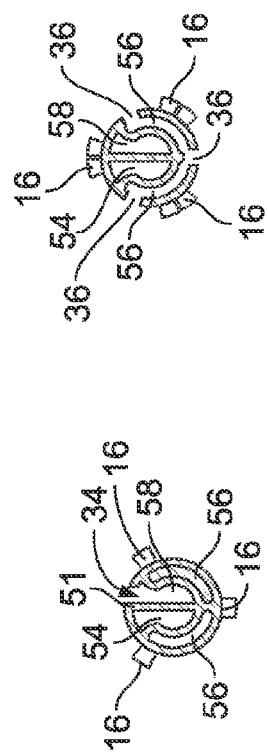
FIG. 7
FIG. 8   FIG. 9   FIG. 10   FIG. 11

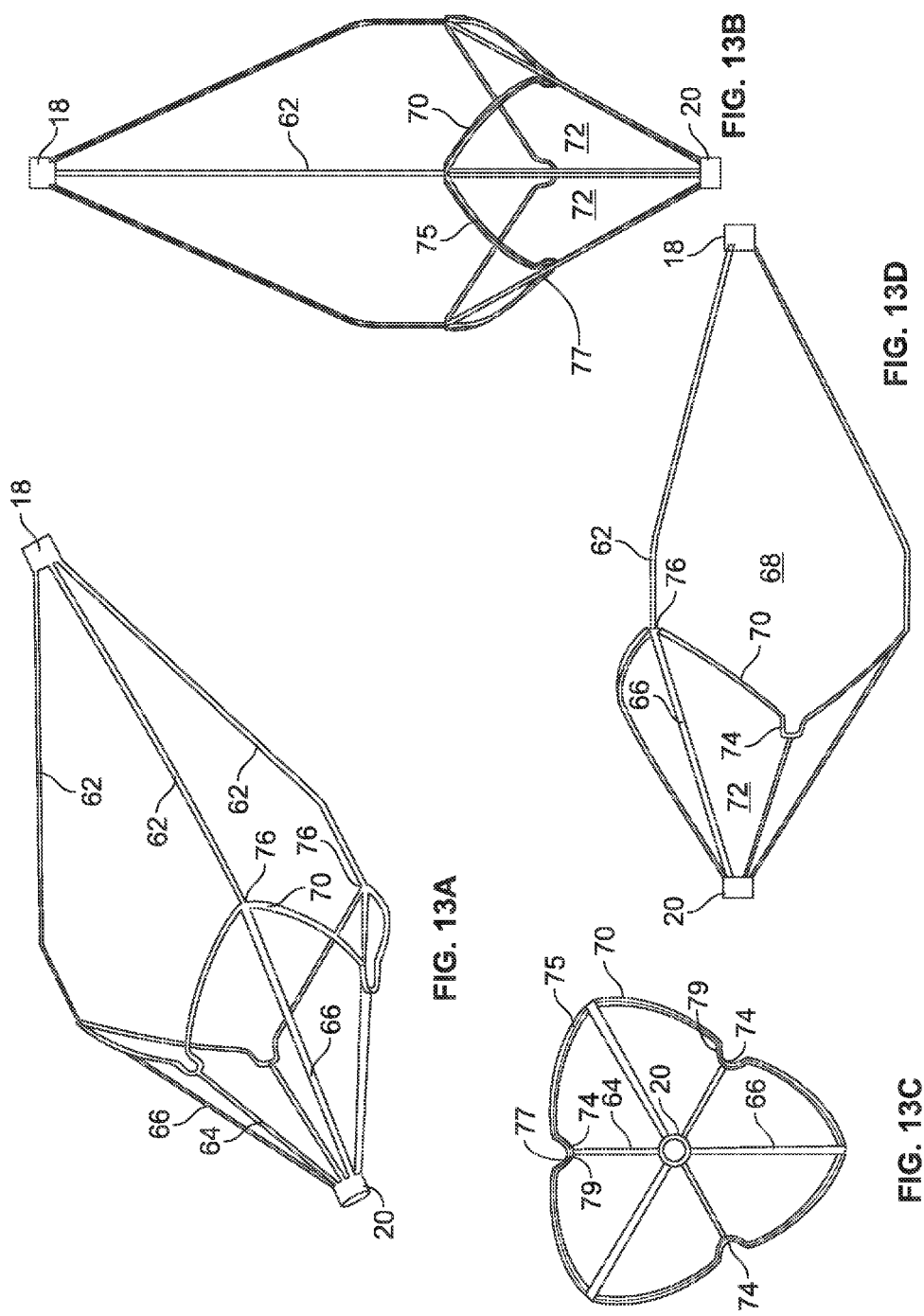

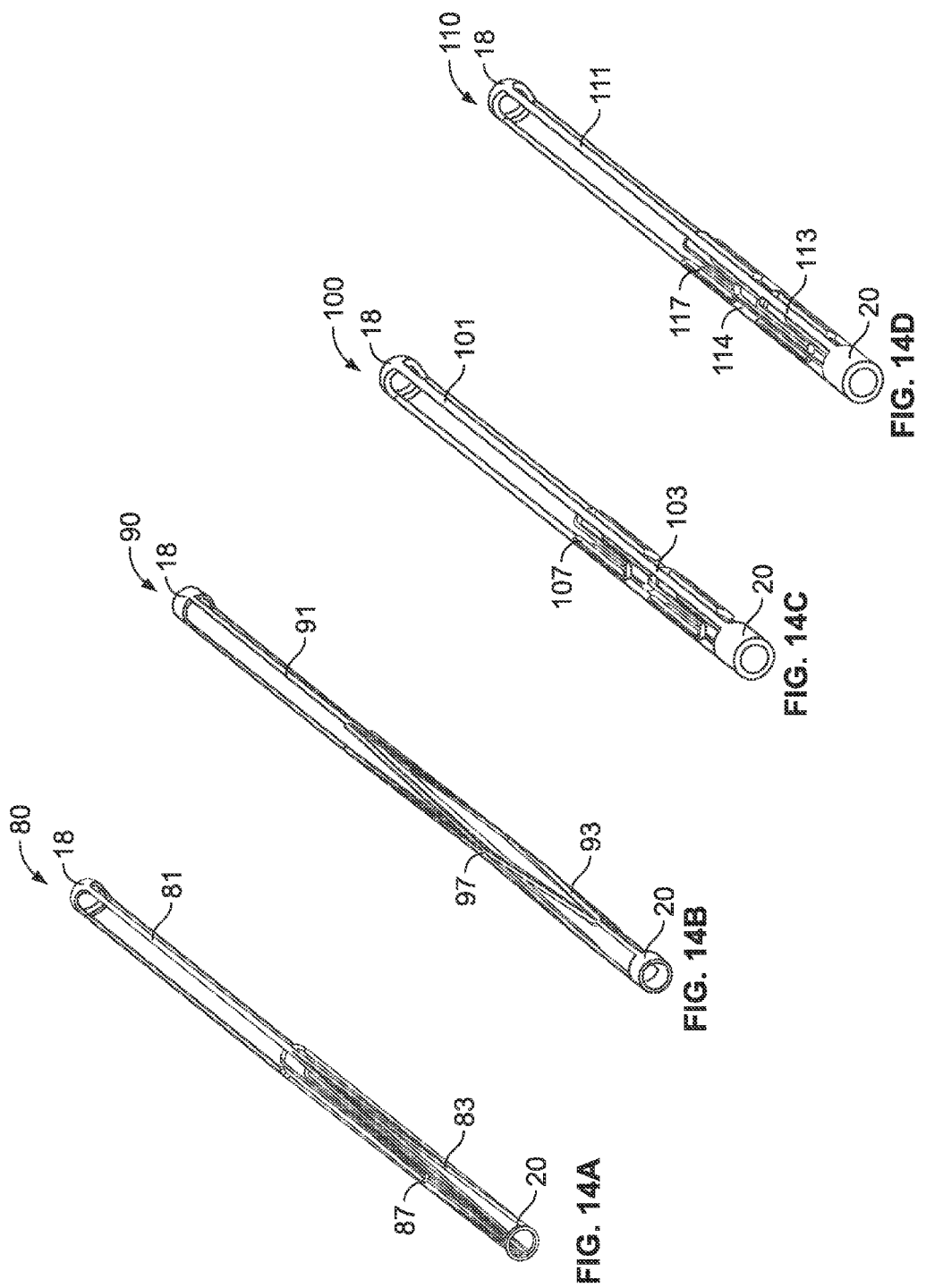

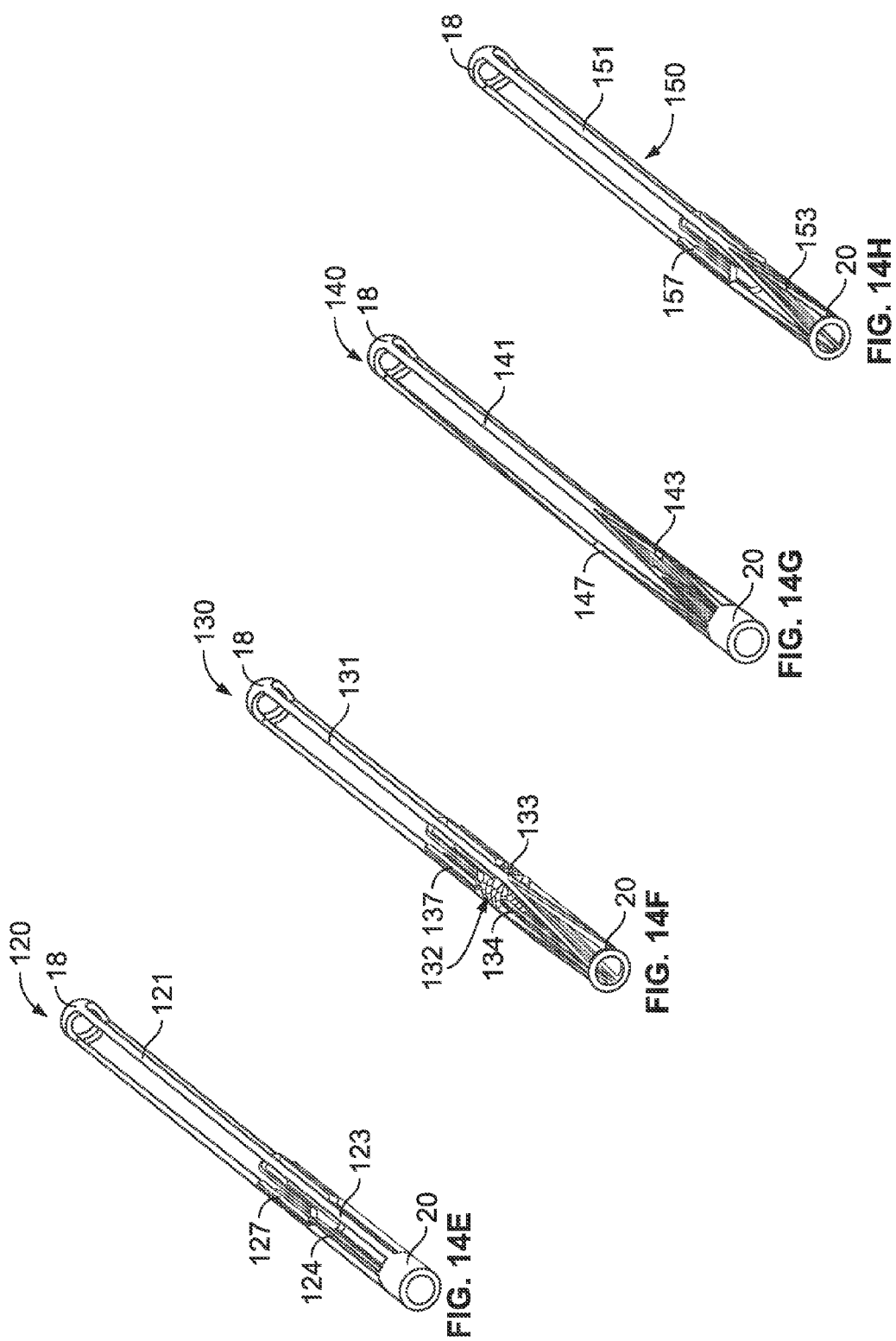

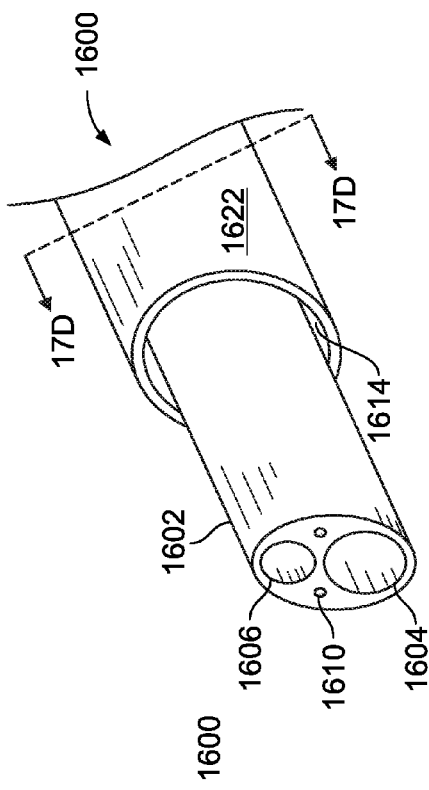
FIG. 18A
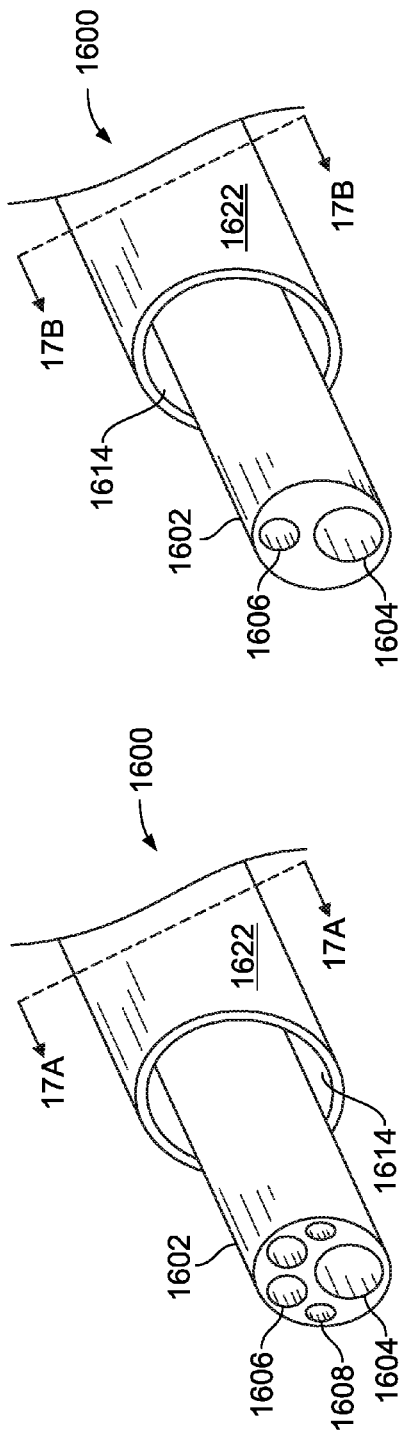
FIG. 18B
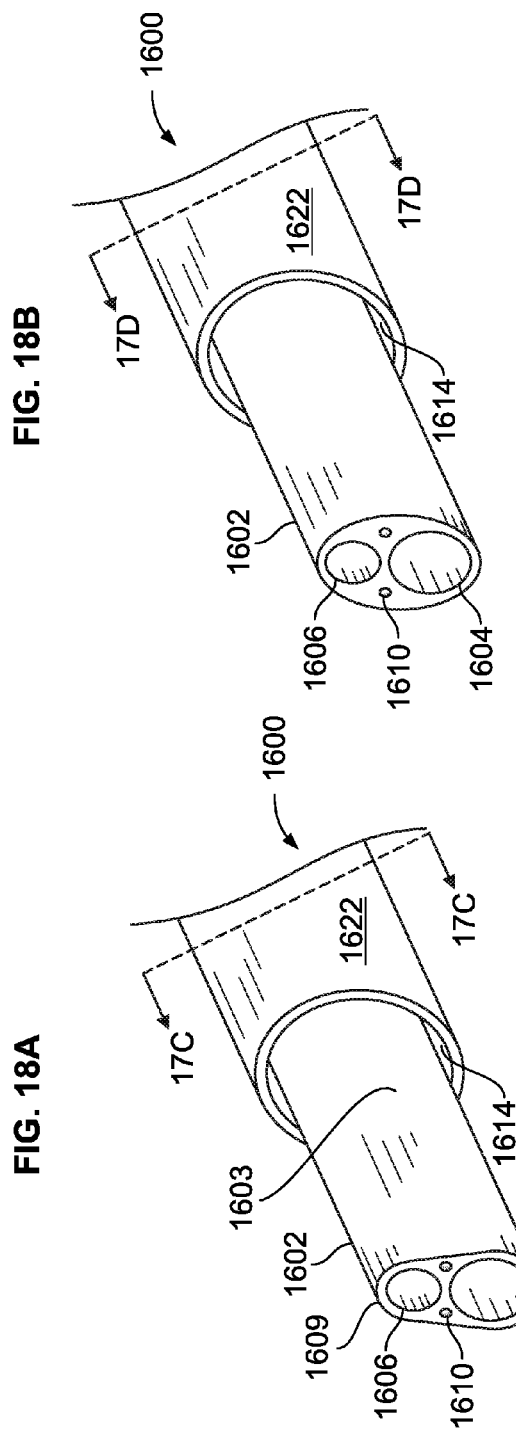
FIG. 18C
FIG. 18D

REDUCED PROFILE CENTRAL VENOUS ACCESS CATHETER WITH VENA CAVA FILTER AND METHOD

CROSS-REFERENCE TO RELATED INVENTIONS

This application is a continuation of and claims priority to U.S. application Ser. No. 13/786,361, filed Mar. 5, 2013, now U.S. Pat. No. 9,687,333; which is a continuation-in-part of U.S. application Ser. No. 11/849,225, filed Aug. 31, 2007, now U.S. Pat. No. 8,668,712; and is also a continuation-in-part of U.S. application Ser. No. 12/684,839, filed Jan. 8, 2010, now U.S. Pat. No. 8,613,753; and is also a continuation-in-part of U.S. application Ser. No. 13/091,826, filed Apr. 21, 2011, now U.S. Pat. No. 8,777,977, each of which is incorporated by reference in its entirety.

BACKGROUND OF THE INVENTION

The present invention pertains generally to the field of vascular filters for capturing embolic material in the blood flow. More particularly, the present invention relates to multi-lumen central venous access catheter of the type typically used for central venous access, and which has a vena cava filter at a distal end. The inventive central venous access vena cava filter catheter also preferably has at least one port generally proximal the filter and at least port distal the filter. The proximal and distal ports provide means for introducing a bioactive agent, such as an anticoagulant or thrombolytic agents, contrast medium, blood transfusions, fluids or medications or as a means for withdrawing blood samples for patient testing.

The present invention may be configured for either a femoral approach or a jugular approach to the inferior vena cava. Vena cava filters are typically deployed infrarenaly, but may also be deployed suprarenaly. It will be understood that within the inferior vena cava blood flow is superior, i.e., toward the patient's head. Thus, in all embodiments, the vena cava filter will be positioned so that it opens inferiorly, i.e., away from the patient's head and toward the direction of the blood flow. It will be appreciated, therefore, that in the present invention, the vena cava filter will have a different axial orientation on the central access catheter depending upon whether the device is intended for use in a femoral approach or a jugular approach.

SUMMARY OF THE INVENTION

The accepted standard of care for patients with venous thromboembolism (VTE) is anticoagulant therapy. Inferior vena cava (IVC) filters are reserved for those patients who fail anticoagulant therapy, or have a complication or contraindication to anticoagulant therapy. Until the early 1970's, the only method of IVC interruption was surgical, either by clipping, ligation or plication. The first clinical experience of an endoluminally-placed device to interrupt IVC flow was reported by Mobin-Uddin et al. in 1969. However, it was not until the introduction of a stainless steel umbrella-type filter by Greenfield et al. in 1973 that an effective method of endoluminally trapping emboli while simultaneously preserving IVC flow became possible. Indeed, for many years, the Greenfield filter set a benchmark by which newer filters were measured. Early generations of filters were inserted by surgical cut-down and venotomy. Eventually filters were able to be inserted percutaneously: initially through large 24 Fr sheaths, though newer generations of filters are able to be delivered through 6 Fr systems.

Despite the safety and efficacy of modern day filters, systemic anticoagulation remains the primary treatment for VTE. Either unfractionated or low molecular weight heparin followed by three months of oral anticoagulation in patients with proximal deep venous thrombosis (DVT) is approximately 94% effective in preventing pulmonary embolism (PE) or recurrent DVT. The routine placement of IVC filters in addition to anticoagulation in patients with documented DVT was investigated by Decousus et al. in a randomized trial. Decousus H, Leizorovicz A, Parent F, et al. *A clinical trial of vena caval filters in the prevention of pulmonary embolism in patients with proximal deep-vein thrombosis*. N Engl J Med 1998; 338:409-415. This study revealed that the use of a permanent filter in addition to heparin therapy significantly decreased the occurrence of PE within the first 12 days compared to those without a filter. However, no effect was observed on either immediate or long-term mortality, and by 2 years, the initial benefit seen in the group of patients with filters was offset by a significant increase in the rate of recurrent DVT.

Despite the efficacy of anticoagulant therapy in the management of VTE, there are certain situations and conditions in which the benefits of anticoagulation are outweighed by the risks of instituting such a therapy. These include contraindications and complications of anticoagulant therapy. In such circumstances, there may be absolute or relative indications for filter insertion Currently, there are at least eight different types of permanent cava filters that are FDA approved. These include the Bird's Nest filter (Cook Incorporated, Bloomington, Ind.), Vena Tech LGM filter (B. Braun, Bethlehem Pa.), Vena Tech LP (B. Braun), Simon Nitinol filter (Bard, Covington, Ga.), Titanium Greenfield filter (Boston Scientific, Natick Mass.), Over-the-Wire Greenfield filter (Boston Scientific), TrapEase filter (Cordis Corp.) and the Gunther Tulip filter (Cook Inc.)

Well-founded concerns over the long-term complications of permanent IVC filters, particularly in younger patients in need of PE prophylaxis with a temporary contraindication to anticoagulation, has led to the development of temporary and retrievable filters. Temporary filters remain attached to an accessible transcutaneous catheter or wire. These have been used primarily in Europe for PE prophylaxis during thrombolytic therapy for DVT. Currently these devices are not approved for use in the United States. Retrievable filters are very similar in appearance to permanent filters, but with modifications to the caval attachment sites and/or hooks at one end that can facilitate their removal. Retrievable filters are currently available in the United States, examples of these include the Gunther Tulip (Cook Inc.), Opt Ease (Cordis Corp.), and Recovery nitinol filters (Bard Peripheral Vascular, Tempe, Ariz.) Lin P H, et al., *Vena caval filters in the treatment of acute DVT. Endovascular Today* 2005; January: 40-50. The time limit of retrievability is in part dependant on the rate of endothelialization of the device, which typically occurs within 2 weeks. However, differences in design may extend the time period in which the filter may be safely retrieved.

Currently no consensus exists as to which patients have an indication for a retrievable filter. However, it is generally accepted that patients at high risk for pulmonary embolism or with documented PE and with a temporary contraindication to anticoagulation are candidates.

Certain circumstances preclude the placement of a filter in the infrarenal IVC. This includes thrombus extending into the infrarenal IVC, renal vein thrombosis or pregnancy. The safety of suprarenal placement of IVC filters is well documented, with no reported instances of renal dysfunction and no differences in the rates of filter migration, recurrent PE or caval thrombosis.

The rate of upper extremity DVT is on the rise. This is predominantly due to an increasing number of patients having short- and long-term upper extremity central venous access catheters. In one study, 88% of patients found to have an upper extremity DVT had a central venous catheter present at the site of thrombosis at the time of diagnosis or within the previous two weeks. Pulmonary embolism may complicate upper extremity DVT in 12-16% of cases. In patients who have such a complication or contraindication to anticoagulation, a filter can be safely placed immediately below the confluence of the brachiocephalic veins. However, misplacement of an SVC filter is theoretically more likely than with an IVC filter because of the relatively short target area for deployment.

The most common imaging modality used for filter insertion is fluoroscopy, performed either in an interventional suite or an operating room. Bedside placement of filters has inherent advantages, particularly for critically ill patients in intensive care settings where transport can be avoided. Portable fluoroscopy, surface duplex ultrasound and intravascular ultrasound (IVUS) have all been used to assist with bedside filter placement.

Vena cava filter placement frequently occurs concomitantly with central access line placement or in critically ill patients that already have a central access line in place. Heretofore, however, there have been no devices which combine the function of a central access catheter and a vena cava filter mounted on the central access catheter to provide both central access and embolic protection.

Accordingly, it is an objective of the present invention to provide a multi-lumen catheter coupled to a vena cava filter that is useful both as a central venous access catheter for administration of intravenous fluids, bioactive agents, contrast agents, flushing agents, pressurized fluids for mechanical thrombolysis and/or withdrawal of blood samples and for capture of thrombus or emboli.

Another aspect of the present invention is to provide a filter geometry in which the proximal portion of the filter, relative to the axis of blood flow, has larger interstitial openings to permit thrombus or embolic material to flow into the filter, while the distal portion of the filter, again relative to the axis of blood flow, has relatively smaller interstitial openings that capture the thrombus or embolic material within the filter. Another way to view this aspect is that the structure of the filter includes a greater open surface area exposed to the flow of embolic material into the filter at its proximal end, while the distal end has smaller open surface area exposed to the flow of embolic material to capture the embolic material in the distal end of the filter member.

BRIEF DESCRIPTION OF THE DRAWINGS

FIG. 2 is a side elevational view of a central venous access vena cava filter catheter in accordance with the first embodiment of the present invention.

FIG. 3. is a cross-sectional view taken along line 3-3 of FIG. 2.

FIG. 4 is a cross-sectional view taken along line 4-4 of FIG. 2.

FIG. 5 is a cross-sectional view taken along line 5-5 of FIG. 2.

FIG. 7 is a side elevational view of a central venous access vena cava filter catheter in accordance with the second embodiment of the present invention.

FIG. 8 is a cross-sectional view taken along line 8-8 of FIG. 7.

FIG. 9 is a cross-sectional view taken along line 9-9 of FIG. 7.

FIG. 10 is a cross-sectional view taken along line 10-10 of FIG. 7.

FIG. 11 is a cross-sectional view taken along line 11-11 of FIG. 7.

FIG. 13A is a perspective view of a vena cava filter member in accordance with a first embodiment thereof.

FIG. 13B is a first side elevational view thereof.

FIG. 13C is an end elevational view thereof.

FIG. 13D is a second side elevational view thereof.

FIGS. 14A-14H are perspective views of alternative embodiments of a vena cava filter member in accordance with the present invention.

FIGS. 18A-18D are perspective views of alternative embodiments of the multi-lumen catheter within the outer sheath in accordance with the present invention.

DETAILED DESCRIPTION OF THE PREFERRED EMBODIMENTS

Figure 16A:
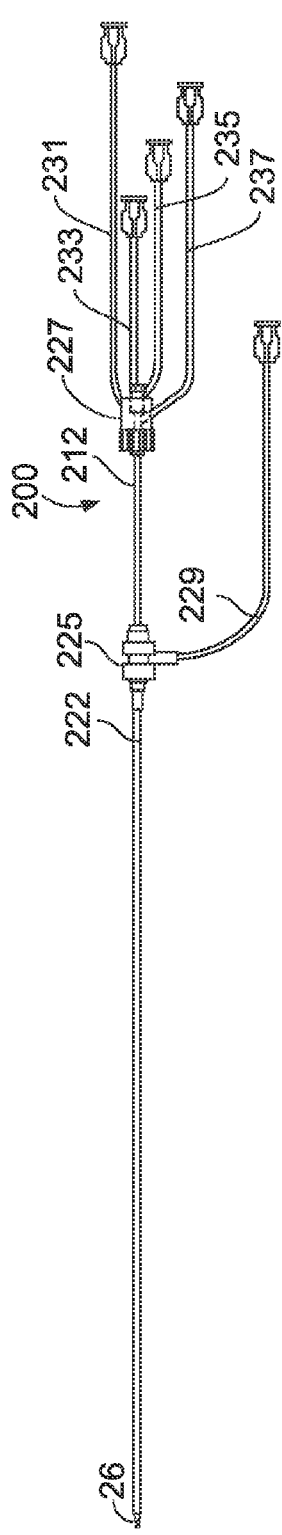
FIG. 16A is a side elevational view of the inventive central access vena cava filter catheter in its undeployed state.
Figure 16B:
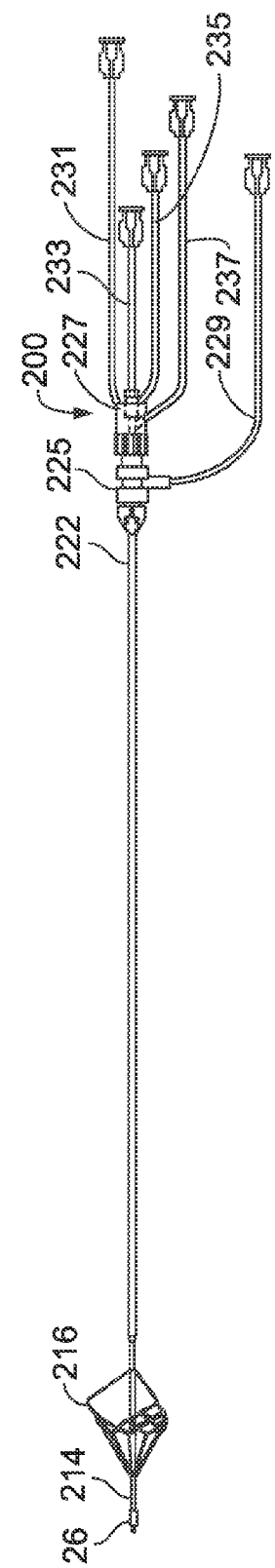
FIG. 16B is a side elevational view of the inventive central access vena cava filter catheter in its deployed state.

In the accompanying Figures like structural or functional elements are designated by like reference numerals, e.g., 16, 116, 216, 316, 416 represent similar structural or functional elements across different embodiments of the invention. With particular reference to FIGS. 1-5, according to a first embodiment of the invention, there is disclosed a central venous access filter ("CVAF") 10 that is composed generally of a multi-lumen central venous access catheter body 12 having a proximal port 32 associated with a first lumen 44 and a distal port 34 associated with a second lumen 42, a filter member 16, having a first end 18 and a second end 20, is positioned generally intermediate the distal port 34 and the proximal port 32 and is generally concentric relative to the catheter body 12. An outer sheath 22 is concentrically disposed over the catheter body 12 such that relative movement of the catheter body 12 and the outer sheath 22 either exposes the filter member 16 or captures the filter member 16 within the outer sheath 22. The outer sheath 22 terminates in an annular opening at a distal end thereof and at first hub member 225 as depicted in FIGS. 16A and 16B. The proximal hub 225 will be described more fully hereinafter. The catheter body 12 extends through a central bore in the proximal hub 225 and passes through a central lumen of the outer sheath 22. A second hub member 227, as depicted in FIGS. 16A and 16B, is coupled to a proximal end of the catheter body 12. The second hub member 227 and the first hub member 225 are removably engageable with each other as will also be described further hereinafter.

Depending upon the orientation of the filter member 16, the first end 18 or the second end 20 may either be fixed or moveable relative to the catheter body 12. Alternatively, as will be discussed further hereinafter, the filter member 16 may have only a first end 18 which is fixed to the catheter body 12

To facilitate percutaneous introduction of the inventive CVAF 10, a physician may optionally elect to employ an outer sheath (not shown) as vascular access conduit for the CVAF 10. The presence of the filter member 16 at the distal end of the catheter body 12 creates a region of relatively lower flexibility and the practitioner may determine it beneficial to employ an outer sheath for vascular access.

As used in this application, unless otherwise specifically stated, the terms "proximal" and "distal" are intended to refer to positions relative to the longitudinal axis of the catheter body 12. Those skilled in the art will understand that the catheter body 12 has a distal end which is first inserted into the patient and a proximal end which opposite the distal end. Additionally, the terms "inferior" or "inferiorly" are intended to refer to the anatomic orientation of being in a direction away from the patient's head while the terms "superior" or "superiorly" are intended to refer to the anatomic orientation of being toward the patient's head.

The multi-lumen aspect of the inventive central venous access filter catheter 10 is shown more clearly in FIGS. 2-5. The catheter body 12 has a proximal section 13 and distal section 14 which has a relatively smaller diametric profile than the proximal section 13. As described above, the first lumen 44 terminates at the proximal port 32, while the second lumen 42 terminates at the distal port 34. A central guidewire lumen 30 may be provided that extends the entire longitudinal length of the catheter body 12 and terminates at the distal end of the catheter body 12 at a distal guidewire opening 31 that permits the catheter body to track along a guidewire during a procedure. The central guidewire lumen 30 may also be used to introduce fluids, such as bioactive agents, intravenous fluids or blood transfusions.

Additionally, at least one of a plurality of infusion lumens 40 are provided, each having at least one infusion port 36 that passes through a wall of the catheter body 12. Bioactive agents, flushing fluids for flushing or under elevated pressures for mechanical thrombolysis of thrombus in the filter member 16, contrast agents or other fluids may be infused through the infusion lumens 40 and out of the at least one infusion port 36 to pass into the patient's venous system for either local or systemic effect. In accordance with one embodiment of the invention, plural infusion ports 36 are provided with multiple ports 36 being provided in communication with a single infusion lumen 40 and spaced along a longitudinal axis of the catheter body 12. Additionally, plural infusion ports 36 may be provided in a circumferentially spaced manner to provide for fluid infusion at points spaced around the circumference of the catheter body 12. In this manner, fluid infusion is provided along both the longitudinal axis and the circumferential axis of the catheter body 12 within the spatial area defined by and bounded by the filter member 16. Because the plural infusion ports 36 communicate with the spatial area defined by and bounded by filter member 16, fluids introduced through the infusion lumens 40 are directed immediately at thrombus caught within the filter member 16. This permits thrombolytic agents, high pressure mechanical thrombolysis using a pressurized saline flush to be introduced directly to the situs of thrombus capture within filter member 16. Alternatively, thermal, ultrasound or other types of thrombolysis may be employed to disrupt thrombus captured by the filter member 16. For example, the annular space between the outer sheath 22 and the catheter body 12 may be used to introduce a thrombolytic to the filter and shower the filter to disrupt thrombus caught by the filter member 16. Additionally, the balloon depicted in FIGS. 21 and 22 may be positioned adjacent the filter member 16 and be provided with plural openings oriented in the direction of the filter member 16 to facilitate thrombolysis.

It will be understood, by those skilled in the art, that alternative arrangements of the first lumen 44, the second lumen 42, the guidewire lumen 30, or the infusion lumens 40 are possible and contemplated by the present invention. The number and arrangement of lumens in the catheter body 12 is a function of the desired number of operable ports passing through the walls of the catheter body 12, the relative position of the operable ports, the desired position and geometry of the guidewire lumen 30, the desired longitudinal flexibility of the catheter body 12, the desirable degree of kink resistance of the catheter body 12, and other factors which are known to one of ordinary skill in the catheter arts.

While the present invention is not limited to specific dimensional sizes of either the catheter body member 12, the outer sheath 22, lumen diameter or port dimension, an exemplary outer diameter size of the outer sheath 22 is between 8 Fr (2.7 mm) and 9 Fr (3.0 mm) while an exemplary outer diameter size of the catheter member 12 is between 6 Fr (2.0 mm) and 7 Fr. A diametric transition taper 15 may be provided between the proximal portion 13 and the distal portion 14 of the catheter body 12 corresponding to the thickness of the filter member 16. In this manner, the outer surface of the filter member 16 is substantially co-planar with the outer diameter of the proximal portion 13 of the catheter body 12 about its entire circumference. Alternatively, the catheter body member 12 may have a constant diameter and the filter member 16 coupled to an outer surface of the catheter body member 12, with the outer sheath 22 having a luminal diameter sufficient to fit over the filter member 16. Moreover, the fixed first end 18 of filter 16 is positioned adjacent and in abutting relationship with the diametric transition 15, while the moveable second end 20 of filter member 16 is concentrically positioned around the distal section 14 of catheter body 12 and is reciprocally moveable thereupon to accommodate diametric expansion of the filter member 16. Lumen diameter and port dimension are a function of design requirements and are variable depending upon the desired purpose and function of the lumen or port, e.g., pressure sensing, infusion, evacuation, guidewire, flow sensing, or flow conduit.

In order to aid a physician in visualizing the CVAF 10 in vivo, at least one radio-opaque or other viewable marker may be provided. A first marker 24 is provided at the distal end of the outer sheath 22 and a second marker 36 may be provided at a distal tip 33 of the catheter body 12. It will be understood that when the outer sheath 22 is in its non-retracted delivery position, that the filter 16 will be covered and the marker 24 and the second marker 36 will be adjacent or in close proximity with one another. Alternatively, the outer sheath 22 may, itself, be made of or include a radio-opaque or other viewable material, such as a metal braid or metal reinforcement within or applied to a polymeric sheath. The first and second markers 24, 36 or the material of the outer sheath 22 may enhance visualization of the CVAF 10 under fluoroscopy, ultrasound or other visualization or guidance technique.

FIGS. 6-11 illustrate a second embodiment of the CVAF 50. Unlike CVAF 10, CVAF 50 does not include the central guidewire lumen 30 of CVAF 10. Rather, while the general construct of CVAF 50 is similar to that of CVAF 10, a different configuration of the inner lumens is employed.

CVAF 50, like CVAF 10, consists generally of a multi-lumen central venous access catheter body 12 having a proximal port 32 associated with a first lumen 54 and a distal port 34 associated with a second lumen 58, a filter member 16, having a fixed proximal end 18 and a moveable distal end 20, is positioned generally intermediate the distal port 34 and the proximal port 32 and is generally concentric relative to the catheter body 12. Use of the term "generally intermediate" with respect to the filter member 16 position is intended to mean that at least a substantial portion of the filter member 16 resides intermediate the distal port 34 and the proximal port 32. Thus, the filter member 16 may partially overlay either or both of the proximal port 32 or the distal port 34.

The catheter body 12 has a proximal section 13 and distal section 14 which has a relatively smaller diametric profile than the proximal section 13. As described above, the first lumen 54 terminates at the proximal port 32, while the second lumen 58 terminates at the distal port 34. An atraumatic tip 52 terminates the catheter body 12 at its distal end. The atraumatic tip 52 preferably includes a radio-opaque marker to aid in positional visualization of the distal end of the catheter body 12.

A plurality of infusion lumens 56 are provided, each having at least one infusion port 36, preferably plural infusion ports 36, that passes through a wall of the catheter body 12 and communicates with a space defined within an area bounded by the filter member 16. Bioactive agents, flushing fluids, pressurized mechanical thrombolytic fluids, or other fluids may be infused through the infusion lumens 56 and out of the at least one infusion port 36 to pass into the space defined by the filter member 16 and ultimately into the patient's venous system for either local or systemic effect. In accordance with one embodiment of the invention, the each of the plural infusion lumens 56 are in fluid communication with plural ports 36 arrayed along both the longitudinal axis and the circumferential axis of the catheter body. This configuration provides for fluid infusion along both the longitudinal axis and the circumferential axis of the catheter body 12 and in direct communication with the space defined by the filter member 16 that captures thrombus.

The infusion lumens 56, the first lumen 54 and the second lumen 58 are bounded by and separated from each other by first catheter septum 51 and second catheter septum 56 which also aid in providing structural support for the catheter body 12. First catheter septum 51 is a generally diametrically and longitudinally extending member that divides the first lumen 54 from the second lumen 58 along the longitudinal axis of the catheter body 12. Second catheter septum 56 may comprise a generally U-shaped member that intersects the first catheter septum 51 at a lower aspect of the septum and is connected with an inner wall surface of the catheter body 12 at upper aspects of the septum 51 to define two infusion lumens in lateral regions of the catheter body 12.

The filter member 16 has two general configurations. A first configuration consists generally of two opposing generally open conical sections formed by plural interconnected structural elements defining the lateral surfaces of each open conical section, wherein the two opposing generally open conical sections each have open bases facing each other which are interconnected by a generally cylindrical section of the filter member 16. Each open conical section has an open base and an apex, wherein the apices project in opposing directions, with one apex projecting proximally and another apex projecting distally relative to the axis of the catheter. The plural interconnected structural elements forming the lateral surfaces of each generally open conical sections may be strut-like structural members extending generally axially along the longitudinal axis of the filter member 16. The axially extending strut-like structural members may be linear members or may be curved members. The apices of each of the generally open conical sections are formed either of a generally cylindrical collar that serves to couple the filter member 16 to the catheter body 12. The generally cylindrical collar is concentrically engaged about the catheter body 12 and may be axially movable thereupon, or is formed by connections between adjacent pairs of longitudinal strut-like structural members which circumscribe a circumference of the catheter body 12. The generally cylindrical section of the filter member 16 is formed by a generally open lattice of interconnected structural elements which connect the base of a first open conical section to the base of a second open conical section. The generally cylindrical section of the filter member 16 lies in apposition with a vascular wall upon deployment of the filter member 16 with a vascular lumen.

A second general configuration of the filter member 16 consists generally of a single generally open conical section in which a plurality of longitudinal strut-like structural members form the lateral surfaces of the conical section and are connected to a generally cylindrical collar which couples the filter member 16 to the catheter body 12 at an apex of the generally open conical section. The base of the generally open conical section is formed by opposing ends of the longitudinal strut-like structural members. A generally cylindrical section of the filter member 16, formed of a generally open lattice of interconnected structural elements, extends from the longitudinal strut-like structural members forming the base of the generally open conical section, to provide a region of the filter member 16 which is in apposition to the vascular wall upon deployment of the filter member.

Figure 1:
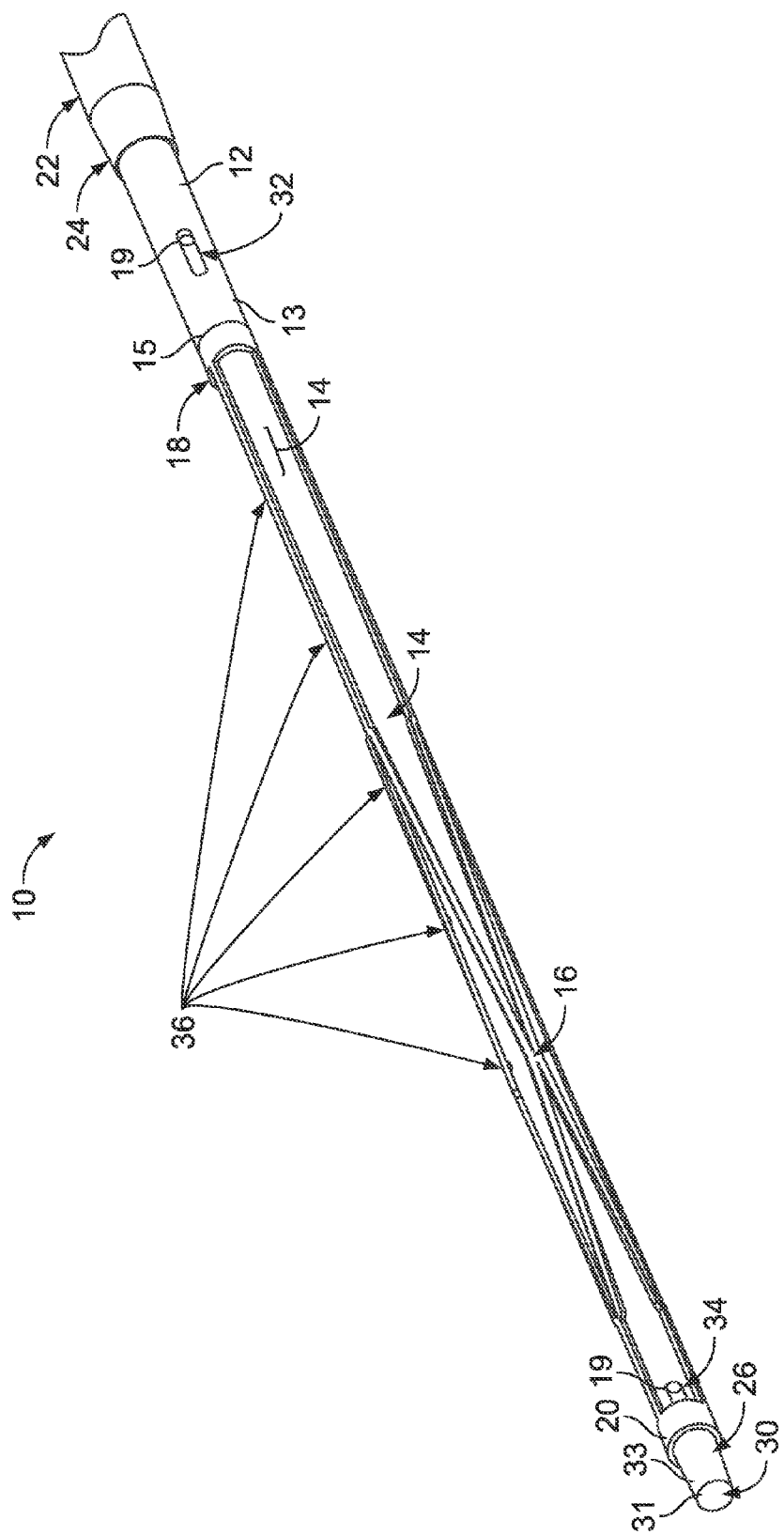
FIG. 1 is a perspective view of a central venous access vena cava filter catheter in accordance with a first embodiment of the present invention with the vena cava filter in an unexpanded state.
Figure 6:
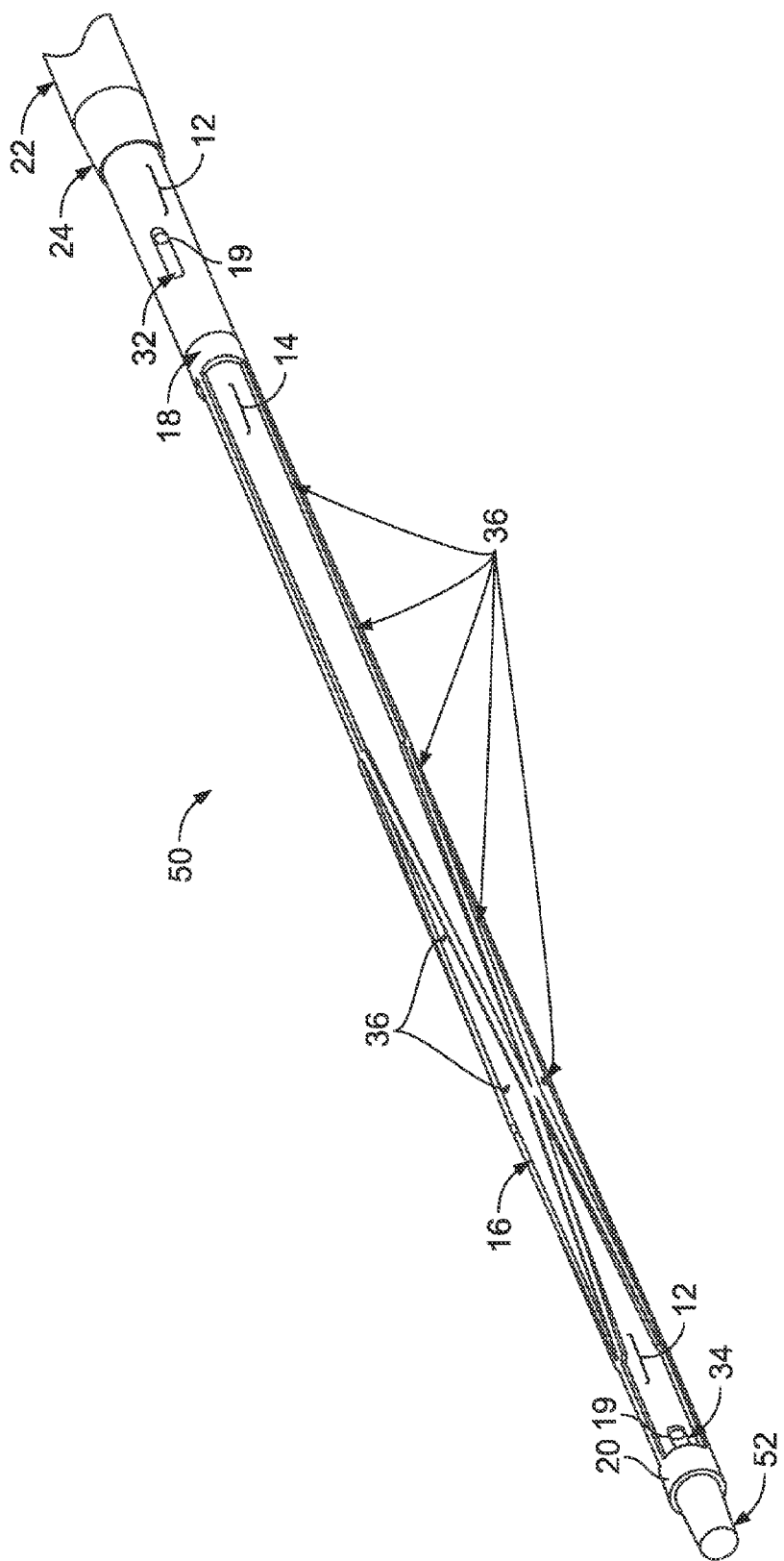
FIG. 6 is a perspective view of a central venous access vena cava filter catheter in accordance with a second embodiment of the present invention illustrating the vena cava filter in an unexpanded state.
Figure 12:
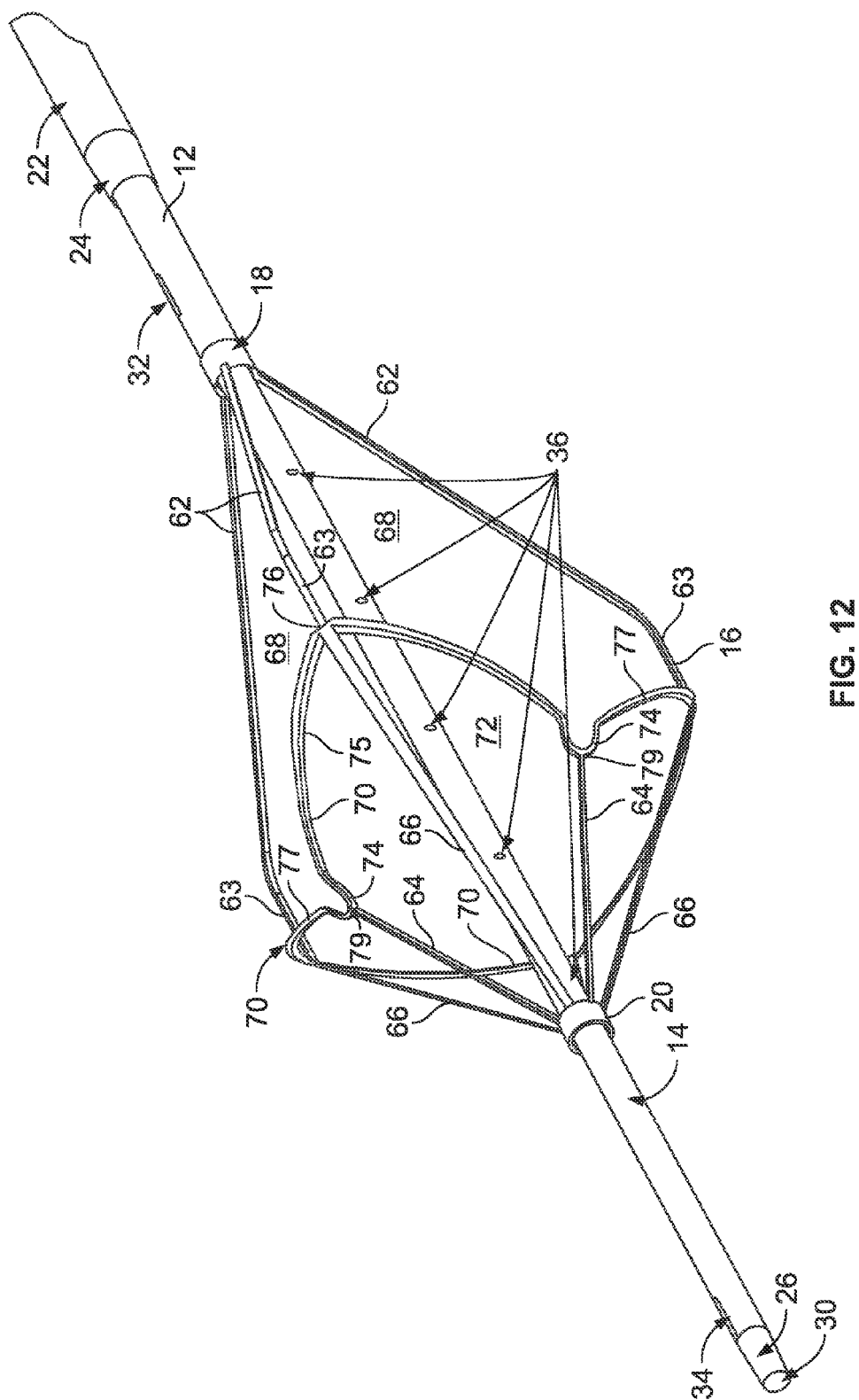
FIG. 12 is a perspective view of the central venous access vena cava filter catheter of FIG. 1 illustrating the vena cava filter in a diametrically expanded state.
Figure 15H:
FIGS. 15A-15H are fragmentary side elevational views of the alternative embodiments of the vena cava filter member illustrated in FIGS. 14A-14H.
Figure 15G:
Figure 15F:
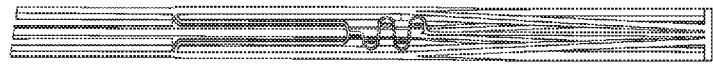
Figure 15E:
Figure 15D:
Figure 15C:
Figure 15B:
Figure 15A:

One embodiment of the filter member 16 is illustrated in its diametrically expanded configuration in FIGS. 12-13D. In this embodiment, filter member 16 consists generally of a first end 18 and a second end 20, each of which consists generally of a tubular structure which is circumferentially positioned about a section of the catheter body 12. One of the first end 18 and second end 20 are fixedly coupled to the catheter body 12, while the other is movable relative to the catheter body 12. At least one of a plurality of first strut members 62, are coupled at their first end to the first end 18 of filter member 16 and each extends axially relative to the longitudinal axis of the catheter body 12. Each of the first strut members 62 is an elongate member that, upon diametric expansion of the filter member 16, flares away from the central longitudinal axis of the catheter body 12, in a generally tapered conical manner, and terminates in an end section 63 that bends generally parallel to and along the longitudinal axis of the catheter body 12. A plurality of second strut members 64 are coupled at an end to the second end 20 of filter member 16 and each extends parallel relative to the longitudinal axis of the catheter body 12. A plurality of third strut members 66 are coupled at ends thereof to the end of the filter member and each extends parallel relative to the longitudinal axis of the catheter body 12. It will be appreciated, by those skilled in the art, that the number of struts employed as the first strut members 62, the second strut members 64 and the third strut members 66 forming the filter member 16 may be evenly distributed about a 360 degree circumference and define the lateral wall surfaces of the filter member 16. A circumferential member 70 extends circumferentially to define a circumferential axis of the filter member 16 and has a series of continuous undulations defining peaks a series of peaks 75 and valleys 77 about the circumference of filter member 16. Each of the plurality of first strut members 62, the plurality of second strut members 64 and the plurality of third strut members 66 are coupled to the circumferential member 70 at different points about its circumferential axis and intermediate the proximal end 18 and the distal end 20 of the filter member 16. In its unexpanded state the filter member 16 has a generally tubular shape, while in its expanded state the filter member 16 assumes one of the general configurations discussed above, i.e., either oppositely extending generally open conical sections or a single generally open conical section.

The plurality of first strut members 62 are preferably offset from each other by approximately 120 degrees about the circumference of the catheter body 12. The plurality of second strut members 64 are also preferably offset from each other by approximately 120 degrees. Finally, the plurality of third strut members 66 are also preferably offset from each other by approximately 120 degrees. Each of the plurality of first strut members 62 couple at a junction 76 to hoop or circumferential member 70 at a peak thereof. Similarly, each of the plurality of third strut members 66 couple at junction 76 to the hoop or circumferential member 70 at a peak thereof. In this manner, a first strut member 62 and a third strut member 66 are each coupled to hoop or circumferential member 70 at junction 76 and, in this relationship, form a generally linear member that extends along the longitudinal axis of the catheter body and connects between the proximal end 18 of the filter member 16 and the distal end 20 of the filter member 16. Each of the second strut members 64 couple, at their proximal ends to a valley 77 of the hoop or circumferential member 70 and connects at a junction 79. Unlike the connections at junction 76 between the plurality of first strut members 62 and the plurality of second strut members, in this embodiment of the filter member 16, there is no member that connects to junction 79 and extends from the proximal end 18 of the filter member 16. In this configuration, the hoop or circumferential member 70 assumes a generally circumferential tri-leaflet ring having three peaks 75 and three valleys 77.

To facilitate bending and folding of the hoop or circumferential member 70 between the expanded and unexpanded states, generally U-shaped hinge members 74 may be provided at each of the valleys 77 of the hoop or circumferential member 70. It will be understood that each of the plurality of first strut members 62, plurality of second strut members 64, plurality of third strut members 66 and the hoop or circumferential member 70 are preferably fabricated of biocompatible materials, such as shape memory alloys, superelastic materials or elastic materials, including, without limitation, titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, cobalt-chromium-molybdenum alloys, nitinol, and stainless steel.

FIGS. 14A-14H and corresponding FIGS. 15A-15H depict alternative embodiments of the filter member 16, labeled 80, 90, 100, 110, 120, 130, 140 and 150, respectively. Like filter member 16, each of filter members 80, 90, 100, 110, 120, 130, 140 and 150 having a proximal end 18 and a distal end 20 that each consist of a generally ring-like structure intended to circumferentially couple to a catheter body 12 (not shown), with the proximal end 18 being fixed and the distal end 20 being reciprocally moveable axially along the distal portion 14 of catheter body 12. Like filter member 16, each of the alternative filter member embodiments depicted in FIGS. 14A-14H and 15A-15H, consist of a plurality of first strut members 81, 91, 101, 111, 121, 131, 141 and 151, respectively, extending distally from the proximal end 18 of the filter member and a plurality of second strut members 83, 93, 103, 113, 123, 133, 143 and 153, respectively, extending proximally from the distal end 20 of the filter member, with a diametrically expansible hoop or circumferential member 87, 97, 107, 117, 127, 137, 147, 157, respectively, interconnecting the distally extending strut members 81, 92, 101, 111, 121, 131, 141 and 151, respectively, with the proximally extending strut members 83, 93, 103, 113, 123, 133, 143 and 153. In the alternative embodiments of filter members 100, 110 and 120, at least some distally extending strut members and at least some of the proximally extending strut members form linear elements that extend along the entire longitudinal axis of the respective filter member, with the hoop or circumferential member being comprised of at least one undulating or serpentine ring structure.

In the alternative embodiments of filter members 80, 90, 130, 140 and 150, a plurality of distally extending strut members are provided spaced approximately 120 degrees apart from one and other about the circumference of the filter members, and the distally extending strut members bifurcating once or twice distally in a generally Y-shaped manner as in filter members 80, 130, 140 or 150, or the proximally extending strut members bifurcating proximally in a generally Y-shaped manner and interconnecting with the distally extending generally Y-shaped strut members to form a diamond-like pattern as in filter member 90. In filter members 90 and 140, the hoop or circumferential member is formed by the diamond-like pattern formed by the intersection of the plurality of struts. In contrast, in filter members 80, 130 and 150, the hoop or circumferential member is formed by at least one undulating or serpentine ring structure which is diametrically expansible. As illustrated in filter members 110, 120 and 130, apical portions of each undulating or serpentine ring structure is interconnected by an interconnecting member 114, 124, 134, respectively, either with an adjacent ring structure, as in filter member 110 or to a distal end 20 of the filter member itself. A longitudinally serpentine section 132 in filter 32 may be provided in conjunction with the interconnecting member 134, to afford greater expansive properties to the hoop or circumferential member 137.

According to some embodiments particularly well-suited for placement by femoral or other infrarenal approach, the filter member 16 is characterized by a generally conical filter member 16 having a greater open surface area exposed to the flow of embolic material into the filter at its proximal end, while the distal end has smaller open surface area exposed to the flow of embolic material to capture the embolic material in the distal end of the filter member.

In other embodiments particularly well-suited for placement by a jugular or suprarenal approach, the filter member 16 is characterized by a generally conical filter member 16 having a greater open surface area exposed to the flow of embolic material into the filter at its distal end, which the proximal end of the filter member 16 has a smaller open surface area exposed to the flow to capture smaller embolic material in the distal end of the filter member 16.

Additionally, in all of the embodiments the filter member 16 is self-centering to provide proper apposition against the vascular walls and centering within the lumen of a blood vessel. This maximizes the flow dynamics of the filter member 16 within the blood vessel for purposes of capturing embolic material within the struts of the filter and centers the catheter body member 12 within the vascular lumen.

As noted above, the proximal 32 and distal 34 ports serve as means for measuring flow rates or pressure differentials across the filter 16. This may be accomplished by including flow sensors and/or pressure transducers 19 in operable association with each port 32, 34, with the associated electrical connections to the flow sensors and/or pressure transducers 19 passing through the respective lumens associated with each port 32, 34 and terminating at the proximal end of the catheter body 12. Where flow sensors 19 are employed, a single flow sensor associated with either proximal port 32 or distal port 34 may be sufficient to detect fluid flow rates at the position of the catheter body 12. Alternatively, the flow sensors and/or pressure transducers 19 may reside in communication with the lumens respectively associated with each port 32, 34 at the proximal end of the catheter body 12, thereby eliminating the need for electrical connectors resident with the associated lumens. Furthermore, wireless flow sensors and/or pressure transducers may be provided in communication with each port 32, 34, and be operably coupled to a power source and a transmitter to wirelessly transmit telemetry data from the transducers to a wireless receiver in communication with the transmitter, as is known in the art.

Alternatively, the proximal 32 and distal ports 34 may be used for monitoring or sensing other conditions in the body that are detectable in the blood. For example, analyte sensors may be introduced to either the lumens communicating with the proximal 32 or distal ports 34 or to the ports themselves to monitor and/or sense chemical or biochemical conditions in the body. An example of this application is monitoring or sampling blood glucose levels for diabetes control. Further, the proximal 32 and distal ports 34 may be used for fluid infusion or for withdrawal or evacuation of fluids or other material through the catheter body 12. In this later instance, where the proximal port 32 is positioned to underlay the filter member 16, thrombus collected in the filter member 16 may capable of being lysed, either by thrombolysis through the infusion ports 36 or under the influence of thermal or mechanical lysis, such as by introducing a laser, ultrasound or other system capable of lysing thrombus, which may be introduced through the lumen communicating with the proximal port 32, or the distal port 32 or the guidewire lumen 30, or introduced separately from the CVAF 10, positioned within the space bounded by the filter member 16, lysing thrombus collected in the filter member 16 and evacuating the lysed thrombus through the proximal port 32

It is known that flow velocity increases proximally within the venous system. For example, a flow rate of 1 L/min is typical in one femoral vein, increases to 2 L/min in the inferior vena cava and increasing another 0.7 to 1 L/min proximate the renal veins. Knowing the typical flow rates coupled with a flow sensor 19 associated with the multi-lumen catheter body 12 may serve to supplement or replace the requirements for fluoroscopy or sonography in placement of the CVAF 10, 50.

Other sensors, such as, for example, chemosensors, color sensors, optical sensors, electrical sensors or biosensors, may be employed in lieu of or in addition to pressure transducer and/or a flow sensor 19 in order to detect other changes or conditions within the patient's vasculature. For example, color sensors exist that sense color changes in thrombus, such color changes may be displayed and interpreted by the medical practitioner as an indication of thrombus staging. Analyte sensors, such a as a glucose sensor or an oxygen saturation sensor may also be employed.

The filter member 16, or its alternative embodiments described above, may be fixed to the catheter body 12 or may be removably coupled to the catheter body 12 for deployment as either a permanent filter or as a temporary and retrievable vena cava filter. Removable coupling of the filter member to the catheter body 12 may be accomplished with a variety of release and retrieval mechanisms operably associated the catheter body 12 and proximate the diametric transition 15. Non-limiting examples of such release and retrieval mechanisms include a wire release that engages with a the proximal end 18 of the filter, a cooperating indexed detent and projection interaction between the catheter body 12 and the proximal end 18 of the filter, such as a detent in the proximal end of the filter and a cooperating projection in the multi-lumen catheter that is positionally indexed to the detent and releasable from the detent, or, alternatively, a helical slot or threads may be formed in the proximal end 18 of the filter and indexed and cooperating projection in the multi-lumen catheter than permits engagement and disengagement with the helical slot or threads.

As depicted in FIGS. 16A and 16B, which depict the undeployed state (FIG. 16A) and the deployed state (FIG. 16B) of the filter member 216, respectively, common to each of the embodiments of the present invention 200 is an inner catheter 214 that carries the vena cava filter 216 at a distal end thereof. The inner catheter 214 is concentrically and reciprocally engaged within an outer sheath 222 such that relative axial movement of the inner catheter 214 and the outer sheath 222 either exposes the vena cava filter 216 for deployment or captures the vena cava filter 216 for retrieval. A first hub member 225 is coupled to a proximal end of the outer sheath 222 and a second hub member 227 is coupled to a proximal end of the inner catheter 214. First hub member 225 and second hub member 227 are engageable, such as by a threaded, bayonet, snap fit, friction fit or interference fit fitting, to secure the inner catheter 214 within the outer sheath 222 and restrict relative axial movement of the two elements after deployment of the vena cava filter 216. A flush line 229 communicates with the first hub member 225 and is in fluid communication with a luminal space within the outer sheath 222. A plurality of fluid lines 231, 233, 235, 237 communicate with the second hub member 227 and are each in fluid communication with one of the plural lumens within the inner catheter member 214, e.g., lumens communicating with the proximal, distal or infusion ports (not shown). A distal tip 26 is provided at a distal end of the inner catheter.

In an alternative embodiment, as depicted in FIGS. 17A-D, the central venous access catheter 1600 comprises a multi-lumen catheter body 1602 and an outer sheath 1622 concentrically disposed about the multi-lumen catheter body 1602. The multi-lumen catheter body 1602 has plural longitudinally extending lumens that pass longitudinally through the catheter body 1602 and are substantially parallel to each other within the catheter body 1602. Each of the plural lumens reside within a single catheter body. The plural lumens define a first lumen 1604 having a first lumen profile. In the embodiment depicted in FIG. 17A, the transverse cross-sectional shape of the multi-lumen catheter body 1602 is circular and the transverse cross-sectional shape of the first lumen profile is also generally circular. In this embodiment, the first lumen 1604 is configured as a central guidewire lumen, permitting a guidewire to pass therethrough.

Figure 17A:
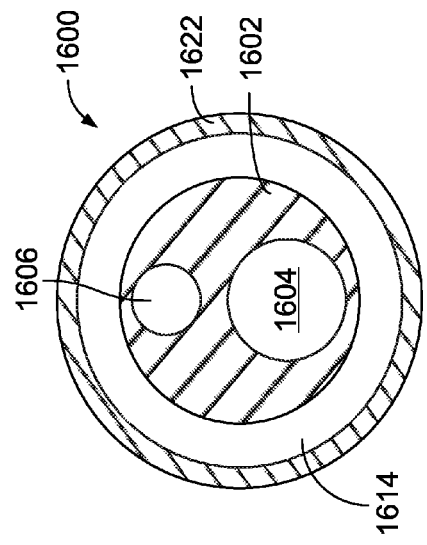
FIGS. 17A-17D are transverse cross-sectional views of alternative configurations of the multi-lumen catheter depicted within an outer sheath and taken along lines 17A-17A, 17B-17B, 17C-17C and 17D-17D of FIGS. 18A-18D respectively.

Also as depicted in the embodiment in FIG. 17A, the multi-lumen catheter body 1602 further defines at least one second lumen 1606 having a second lumen profile that is different than the first lumen profile. In this embodiment, the second lumen profile is again generally circular and has a diameter that is not equal to the diameter of the first lumen profile. In this embodiment, the diameter of the second lumen profile is less than the diameter of the first lumen profile. The second lumen 1606 is configured to permit fluid flow therethrough. As depicted in FIG. 17A, two or more second lumens 1606 may be provided in the multi-lumen catheter body 1602, with the second lumens 1606 being positioned laterally adjacent and parallel each other within the multi-lumen catheter body 1602.

The multi-lumen catheter body 1602 embodiment depicted in FIG. 17A further comprises a third lumen 1608 that has a third lumen profile that is different from at least one of the first lumen profile and the second lumen profile. In this embodiment, the third lumen profile is different from both the first lumen profile and the second lumen profile. Furthermore, the third lumen profile is generally circular. In this embodiment, the third lumen profile has a diameter that is less than the diameters of both the first lumen profile and the second lumen profile. The third lumen 1608 is configured to permit either a reinforcing member to be disposed therethrough or to permit fluid flow therethrough.

Figure 17B:
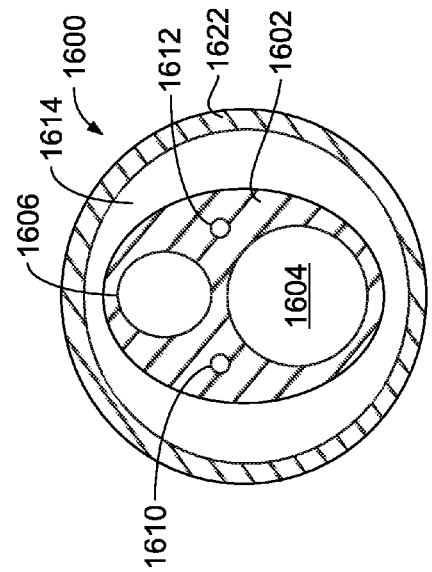

FIG. 17B depicts an embodiment of the central access vena cava filter catheter 1600 similar in general configuration as that depicted in FIG. 17A, except that the multi-lumen catheter body 1602 only has a first lumen 1604 and a second lumen 1606 passing longitudinally therethrough. Again, the transverse cross-sectional shape of the multi-lumen catheter body 1602 is generally circular, as is the transverse cross-sectional shape of the lumen profiles of each of the first lumen 1604 and the second lumen 1604. Also, as with the embodiment depicted in FIG. 17A, the diameter of first lumen 1604 is different than the diameter of the second lumen 1606, in this case, as depicted, the diameter is smaller than that of the second lumen 1606.

Figure 17C:
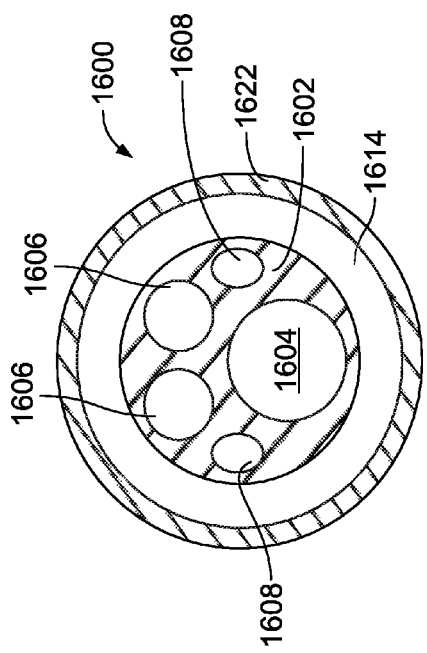

FIG. 17C depicts an alternative embodiment of the central access vena cava filter catheter 166 in which the transverse cross-sectional shape of the multi-lumen catheter body 1602 is non-circular, and has two generally planar and elongate side walls 1603 and 1605 and two generally curved or radiused walls 1607 and 1609 that connect each of the elongate side walls 1603 and 1605 at both ends thereof. In this embodiment, the elongate side walls 1603 and 1605 are non-parallel to each other, such that the radius of curvature R1 of one radius wall 1609 is less than the radius of curvature R2 of the second radius wall 1607. This configuration permits the first lumen 1604 to have a larger diameter than that of the second lumen 1606. It will be understood, however, by those skilled in the art, that the elongate side walls 1603 and 1605 may be configured to be parallel to each other and that the radius walls having the same radius of curvature such that R1 is equal to R2. In this later case, the first lumen 1604 and the second lumen 1606 may still have different diameters or may be configured to have like diameters.

In the embodiment depicted in FIG. 17C, at least one and, preferably two, fourth lumens 1610 are provided that pass longitudinally through the multi-lumen catheter body 1602 and are parallel to each other and to the first 1604 and second 1606 lumens. In this case, the two fourth lumens 1610 are disposed laterally separated from each other along a plane P1 that is generally intermediate the first 1604 and second 1606 lumens and resides within the multi-lumen catheter body 1602 and not intersecting with either of the first 1604 or second 1606 lumens. As with the third lumen 1608 depicted in FIG. 17A, the fourth lumen 1610 may be used to retain a reinforcing member therein.

Figure 17D:
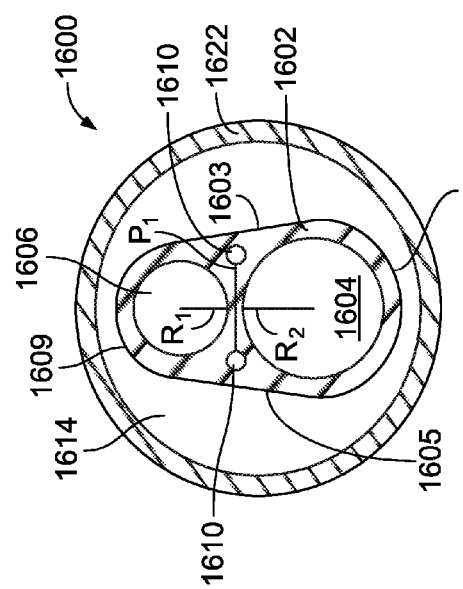

Finally, as depicted in FIG. 17D, the transverse cross-sectional shape of the multi-lumen catheter body 1602 is generally ovular. As with the embodiments in FIG. 17B and FIG. 17C, a first lumen 1604 and a second lumen 1606 pass longitudinally through the multi-lumen catheter body and are parallel to each other. The transverse cross-sectional shapes of the first lumen 1604 and the second lumen 1606 are generally circular and may have equal or unequal diameters. Like with the embodiment depicted in FIG. 17C, there is provided at least one and, preferably two, fourth lumens 1610 are provided that pass longitudinally through the multi-lumen catheter body 1602 and are parallel to each other and to the first 1604 and second 1606 lumens. In this case, the two fourth lumens 1610 are disposed laterally separated from each other along a plane P1 that is generally intermediate the first 1604 and second 1606 lumens and resides within the multi-lumen catheter body 1602 and not intersecting with either of the first 1604 or second 1606 lumens. Again, as with the third lumen 1608 depicted in FIG. 17A, the fourth lumen 1610 may be used to retain a reinforcing member therein.

The third lumen 1608 or the fourth lumen 1610, depending upon the embodiment, is configured to permit a reinforcing member to be disposed therethrough. The reinforcing member adds longitudinal strength to the multi-lumen catheter body member 1602 to add both column strength to aid in pushability of the multi-lumen catheter body member 1602 and to add elongation strength to the multi-lumen catheter body member to aid in resisting longitudinal stretching of the material of the multi-lumen catheter body during re-positioning or withdrawal from the patient.

The reinforcing member is preferably a wire that is either disposed within the third lumen 1608 or the fourth lumen 1610 or is co-extruded with the multi-lumen catheter body 1602. It is preferable that the reinforcing member be fabricated of a biocompatible material, such as stainless steel, shape memory alloy, superelastic materials or elastic materials, including, without limitation, titanium, vanadium, aluminum, nickel, tantalum, zirconium, chromium, silver, gold, silicon, magnesium, niobium, scandium, platinum, cobalt, palladicum, manganese, molybdenum and alloys thereof, such as zirconium-titanium-tantalum alloys, cobalt-chromium-molybdenum alloys, nickel-titanium alloys or the like. The reinforcing member may have a surface profile such as threads, raised structures, grooves, detents, depressions, or the like, to aid in securing the reinforcing member within the third lumen 1608 or the fourth lumen 1610.

While the multi-lumen catheter body 1602 is depicted in FIGS. 17A-17D and 18A-18D, with the illustrated transverse cross-sectional shapes, it will be understood that alternative transverse cross-sectional shapes are envisioned by the present invention, including, without limitation, polygonal shapes, elliptical shapes, or complex curvilinear shapes, such as petals about a central axis or the like.

The central access venous catheter 1600 further comprises an outer sheath 1622 disposed substantially concentrically about the outside of the multi-lumen catheter body 1602 thereby forming a fluid passageway 1614. In the instant embodiment, due to the shape of the body profile, the fluid passageway 1614 may be annular as depicted in FIGS. 17A and 17B or non-annular as depicted in FIGS. 17C and 17D. It will be understood that the fluid passageway 1614 has a large cross-sectional surface area and is well suited for infusing larger volumes of fluid to the distal end of the central access venous catheter 1600 than that possible through any of the first, second, third or fourth lumens.

Finally, each if the first lumen 1604, the second lumen 1606, the third lumen 1608 and the fourth lumen 1610 extend to a distal aspect of the multi-lumen catheter body and open at a distal aspect of the multi-lumen catheter body. The first lumen 1604, when used as a guidewire lumen, will extend the entire longitudinal length of the inventive central access vena cava filter catheter 1600 and open, in fluid flow communication, at substantially a very distal end of the catheter 1600. The second lumen 1606 may extend to a point generally proximal to the position of the vena cava filter member 14 and be skived or otherwise open in fluid flow communication through a side wall of the multi-lumen catheter body member 1602 to permit fluid flow to exist a distal end of the second lumen 1606. When used for fluid flow, the third lumen 1608 or the fourth lumen 1610 may terminate in a skive or be otherwise open in fluid flow communication through a side wall of the multi-lumen catheter body member 1602 to permit fluid flow to exit the multi-lumen catheter body 1602. When used to retain a reinforcing member, the third lumen 1608 and the fourth lumen 1610 will preferably extend a substantial aspect of the multi-lumen catheter body member 1602 to afford maximal reinforcing capacity. Finally, the fluid passageway 1614 being defined between outer sheath 1622 and the multi-lumen catheter body 1602, will terminate and be open at a distal end of the outer sheath 1622, the position of which relative to the multi-lumen catheter body 1602 is variable.

Thus, there has been described a central venous access filter in accordance with the foregoing embodiments of the invention which include, generally, a multi-lumen catheter body, a filter member and an introducer sheath. The multi-lumen catheter body has a plurality of ports each of which are in fluid flow communication with at least one lumen in the multi-lumen catheter body. Lumens may include a central guidewire lumen useful for tracking over a guidewire and/or larger volume infusion of bioactive agents, intravenous fluids, blood transfusions, or other fluids; infusion lumens in communication with infusion ports positioned to direct fluids to the space bounded by the filter member for introducing bioactive agents, including thrombolytic agents or flushing agents, including pressurized fluids for mechanical thrombolysis directly to the capture site of the thrombus in the filter member; and lumens communicating with proximal and distal ports which may also be used for fluid introduction and/or may house or communicate with sensors, such as pressure transducers, flow sensors, analyte sensors, color sensors, optical sensors or the like. The filter member may be detachable from the multi-lumen catheter body to permit temporary filter placement and later retrieval by a detachment mechanism that cooperates between the filter and the multi-lumen catheter body. These and other aspects of the present invention are provided by way of non-limiting examples, with the claims appended hereto serving to define the scope of the subject matter regarded as the invention.

What is claimed is:

1. A multi-lumen catheter comprising a single catheter body member, wherein the body member has a generally transverse cross-sectional shape having generally planar lateral side walls, a first curvilinear surface connecting one end of the two generally planar lateral side walls and a second curvilinear surface connecting a second end of the two generally planar lateral side walls;

the single catheter body member having formed therein a first lumen having a first transverse lumen profile and a second lumen having a second transverse lumen profile different from the first transverse lumen profile;

wherein each of the first lumen and the second lumen spaced apart and parallel relative to each other within the single catheter body member and each have a proximal opening and a distal opening such that fluid flow may pass therethrough; and a sheath disposed about at least a longitudinal portion of the single catheter body member, in spaced apart relationship with the single catheter body member forming a fluid passageway between an inner surface of the sheath and an outer surface of the single catheter body member.

2. The multi-lumen catheter of claim 1, further comprising a third lumen having a third lumen profile different from each of the first lumen profile and the second lumen profile, the third lumen being spaced apart and parallel relative to each of the first lumen and the second lumen within the single catheter body and the third lumen having a proximal and a distal opening such that either a reinforcing member may be disposed and retained therethrough or fluid flow may pass therethrough.

3. The multi-lumen catheter of claim 2, wherein each of the first transverse lumen profile, the second transverse lumen profile and the third transverse lumen profile have a generally circular transverse cross-sectional profile.

4. The multi-lumen catheter of claim 2, further comprising a fourth lumen having a fourth transverse lumen profile.

5. The multi-lumen catheter of claim 4, wherein the fourth transverse lumen profile is similar to the third transverse lumen profile.

6. The multi-lumen catheter of claim 4, wherein the fourth lumen has a proximal and a distal opening such that either a reinforcing member may be disposed and retained therethrough or fluid flow may pass therethrough.

7. The multi-lumen catheter of claim 1, wherein the fluid passageway is generally annular.

8. The multi-lumen catheter of claim 7, wherein the fluid passageway is generally non-annular.

9. The multi-lumen catheter of claim 1, wherein the first curvilinear surface has a radius less than the second curvilinear surface.

10. The multi-lumen catheter of claim 1, wherein first lumen and the second lumen are generally circular in transverse cross-sectional shape and the first lumen has a diameter less than a diameter of the second lumen.

11. The multi-lumen catheter of claim 1, further comprising a vena cava filter member disposed concentrically about a distal end of the single catheter body member.

12. The multi-lumen catheter of claim 11, wherein the sheath is concentrically disposed about the vena cava filter member and reciprocally moveable relative thereto.

13. The multi-lumen catheter of claim 12, wherein the fluid passageway terminates proximal the vena cava filter member when the sheath is in a retracted state and distal the vena cava filter member when the sheath is in an extended state.

14. The multi-lumen catheter of claim 11, wherein the distal opening of the first lumen terminates proximal the vena cava filter member.

15. The multi-lumen catheter of claim 14, wherein the distal opening of the second lumen terminates distal the vena cava filter member.

16. The multi-lumen catheter of claim 11, further comprising a third lumen having a third lumen profile different from each of the first lumen profile and the second lumen profile, the third lumen being spaced apart and parallel relative to each of the first lumen and the second lumen within the single catheter body and the third lumen having a proximal and a distal opening such that either a reinforcing member may be disposed and retained therethrough or fluid flow may pass therethrough;

further wherein the distal opening of the third lumen terminates in a plurality of openings arrayed along a longitudinal and circumferential axis of the single catheter body member and positioned between a proximal end and a distal end of the vena cava filter member.

17. The multi-lumen catheter of claim 11, wherein the vena cava filter member is fixedly attached to the single catheter body member at a first end of the vena cava filter member and is reciprocally movable relative to the single catheter body member at a second end of the vena cava filter member.

18. The multi-lumen catheter of claim 11, wherein the vena cava filter member is asymmetric along its longitudinal axis.

* * * * *